(12) United States Patent
Makabe et al.

(10) Patent No.: US 9,073,854 B2
(45) Date of Patent: Jul. 7, 2015

(54) AROMATIC SULFONIUM SALT COMPOUND

(75) Inventors: Yoshie Makabe, Tokyo (JP); Yuta Okuyama, Tokyo (JP)

(73) Assignee: ADEKA CORPORATION, Tokyo (JP)

( * ) Notice: Subject to any disclaimer, the term of this patent is extended or adjusted under 35 U.S.C. 154(b) by 434 days.

(21) Appl. No.: 13/389,821

(22) PCT Filed: Nov. 17, 2010

(86) PCT No.: PCT/JP2010/070469
§ 371 (c)(1),
(2), (4) Date: Feb. 10, 2012

(87) PCT Pub. No.: WO2011/062182
PCT Pub. Date: May 26, 2011

(65) Prior Publication Data
US 2012/0136155 A1    May 31, 2012

(30) Foreign Application Priority Data
Nov. 17, 2009    (JP) ................................ 2009-262367

(51) Int. Cl.
C07D 219/06 (2006.01)
C08F 2/50 (2006.01)
G03F 7/004 (2006.01)
C08G 59/68 (2006.01)
C08L 63/00 (2006.01)

(52) U.S. Cl.
CPC ............... C07D 219/06 (2013.01); C08F 2/50 (2013.01); G03F 7/0045 (2013.01); C08G 59/68 (2013.01); C08L 63/00 (2013.01)

(58) Field of Classification Search
CPC .......... C07D 219/06; C08F 2/50; C08G 59/68
USPC ........................................................ 546/103
See application file for complete search history.

(56) References Cited

U.S. PATENT DOCUMENTS

| | | | |
|---|---|---|---|
| 4,324,628 A | 4/1982 | Avar et al. | |
| 6,054,501 A * | 4/2000 | Taniguchi et al. | 522/31 |
| 6,280,859 B1 | 8/2001 | Onikubo et al. | |
| 6,368,769 B1 | 4/2002 | Ohkawa et al. | |
| 2001/0033944 A1 | 10/2001 | Onikubo et al. | |

FOREIGN PATENT DOCUMENTS

| | | |
|---|---|---|
| CH | 643538 | 6/1984 |
| CN | 1195356 | 10/1998 |
| JP | 09-143212 | 6/1997 |
| JP | 09-157350 | 6/1997 |
| JP | 10-251633 | 9/1998 |
| JP | 2000-186071 | 7/2000 |
| WO | WO 97/47660 | 12/1997 |

OTHER PUBLICATIONS

Bioisosteres, Patani et al 1996.*
International Search Report, PCT/JP2010/070469, Dec. 21, 2010.
Yonglie Chen et al., Radiation-curable materials and application, p. 158, Chemical Industry Press, Beijing, 2003.
Extended European Search Report dated Feb. 15, 2013 in corresponding European Patent Application No. 10831576.3.

* cited by examiner

Primary Examiner — Rita Desai
(74) Attorney, Agent, or Firm — Young & Thompson

(57) ABSTRACT

Disclosed are a photo-acid generator having high developing properties, a cationic polymerization initiator having high curing properties, and a resist composition and a cationically polymerizable composition containing the photo-acid generator and the cationic polymerization initiator, respectively. Described are a noble aromatic sulfonium salt compound of general formula (I) and a photo-acid generator, a cationic polymerization initiator, a resist composition, and a cationically polymerizable composition containing the compound.

In formula (I), $R^1$ to $R^{10}$ are each an optionally substituted C1-C18 alkyl, etc.; $R^{11}$ to $R^{17}$ are each an optionally substituted C1-C18 alkyl, etc.; $R^{18}$ is an optionally substituted C1-C18 alkyl, etc.; and $X_1^{31}$ is a monovalent anion.

8 Claims, No Drawings

AROMATIC SULFONIUM SALT COMPOUND

TECHNICAL FIELD

This invention relates to a noble aromatic sulfonium salt compound and more particularly to an aromatic sulfonium salt compound, a photo-acid generator and a cationic polymerization initiator each containing the compound, and a resist composition and a cationically polymerizable composition containing the photo-acid generator or the cationic polymerization initiator, respectively.

BACKGROUND ART

A sulfonium salt compound is a substance that generates an acid on exposure to energy radiation, such as light, and is used, for example, as a photo-acid generator in photolithographic resist compositions used in the formation of electronic circuits having semiconductors or as a cationic polymerization initiator in photopolymerizable compositions, such as stereolithographic resin compositions, paint, coatings, and adhesives.

Patent Literatures 1 to 3 below each disclose an aromatic sulfonium salt compound, a photo-acid comprising the compound, and a photopolymerizable composition containing the photo-acid generator. However, the photo-acid generators disclosed are insufficient in developing properties and when, in particular, used as a negatively working resist, have difficulty in micropatterning.

PRIOR ART DOCUMENT

Patent Literature

Patent Literature 1: JP 9-143212A
Patent Literature 2: JP 9-157350A
Patent Literature 3: 2000-186071A

SUMMARY OF THE INVENTION

Problem to be Solved by the Invention

An object of the invention is to provide a photo-acid generator having high developing properties and a cationic polymerization initiator achieving high curing properties.

Another object of the invention is to provide a resist composition and a cationically polymerizable composition containing the photo-acid generator or the cationic polymerization initiator.

Means for Solving the Problem

As a result of extensive investigations, the inventors have found that an aromatic sulfonium salt compound having a specific structure accomplishes the above objects and thus reached the invention.

The invention provides a novel aromatic sulfonium salt compound represented by general formula (I):

[Chem. 1]

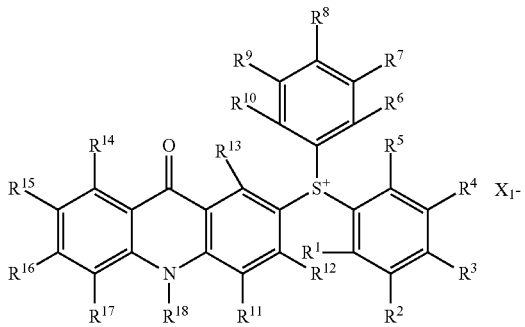

(I)

wherein $R^1$, $R^2$, $R^3$, $R^4$, $R^5$, $R^6$, $R^7$, $R^8$, $R^9$, and $R^{10}$ each independently represent a hydrogen atom, a halogen atom, a hydroxyl group, a nitro group, an optionally substituted alkyl group having 1 to 18 carbon atoms, an optionally substituted aryl group having 6 to 20 carbon atoms, or an optionally substituted arylalkyl group having 7 to 20 carbon atoms;

$R^{11}$, $R^{12}$, $R^{13}$, $R^{14}$, $R^{15}$, $R^{16}$, and $R^{17}$ each independently represent a hydrogen atom, a halogen atom, a hydroxyl group, a nitro group, or an optionally substituted alkyl group having 1 to 18 carbon atoms;

$R^{18}$ represents a hydrogen atom, an optionally substituted alkyl group having 1 to 18 carbon atoms, an optionally substituted aryl group having 6 to 20 carbon atoms, or an optionally substituted arylalkyl group having 7 to 20 carbon atoms;

the number of optional substituents when present on the C1-C18 alkyl group represented by $R^1$ through $R^{18}$, the C6-C20 aryl group represented by $R^1$ through $R^{10}$ and $R^{18}$, and the C7-C20 arylalkyl group represented by $R^1$ through $R^{10}$ and $R^{18}$ being not limited;

the methylene chain of the C1-C18 alkyl group represented by $R^1$ through $R^{18}$, the C6-C20 aryl group represented by $R^1$ through $R^{10}$ and $R^{18}$, and the C7-C20 arylalkyl group represented by $R^1$ through $R^{10}$ and $R^{18}$ being optionally interrupted by —O—, —S—, —CO—, —CO—O—, or —O—CO—; and $X_1^-$ represents a monovalent anion.

The invention also provides a photo-acid generator comprising the aromatic sulfonium salt compound.

The invention also provides a resist composition containing the photo-acid generator.

The invention also provides a cationic polymerization initiator comprising the aromatic sulfonium salt compound.

The invention also provides a cationically polymerizable composition containing the cationic polymerization initiator.

Effect of the Invention

The aromatic sulfonium salt compound provides a photo-acid generator having high developing properties. A photoresist or a photopolymerizable composition containing the photo-acid generator exhibits high sensitivity and achieves high resolution and is therefore useful as a negative resist sensitive to radiation, such as UV light, electron beam, or X rays, and useful in the fabrication of semiconductor integrated circuits, TFT circuits for LCDs, and masks for circuit formation.

The aromatic sulfonium salt compound of the invention is also useful as a cationic polymerization initiator and provides a cationically polymerizable composition exhibiting excellent curability.

BEST MODE FOR CARRYING OUT THE INVENTION

The invention will be described in detail based on its preferred embodiments. The aromatic sulfonium salt compound of the invention which is represented by general formula (I) will be described first.

Examples of the halogen represented by $R^1$ to $R^{17}$ in formula (I) include fluorine, chlorine, bromine, and iodine.

Examples of the optionally substituted C1-C18 alkyl represented by $R^1$ to $R^{18}$ in formula (I) include methyl, ethyl, propyl, isopropyl, butyl, s-butyl, t-butyl, isobutyl, amyl, isoamyl, t-amyl, hexyl, cyclohexyl, isohexyl, 2-ethylhexyl, heptyl, octyl, nonyl, decyl, undecyl, dodecyl, tridecyl, isotridecyl, tetradecyl, hexadecyl, heptadecyl, octadecyl, 1-adamantyl, 2-adamantyl, 2-methyl-1-adamantyl, 2-methyl-2-adamantyl, 2-ethyl-1-adamantyl, 2-ethyl-2-adamantyl, 2-norbornyl, 2-norbornylmethyl, vinyl, allyl, isopropenyl, 1-propenyl, fluoromethyl, difluoromethyl, trifluoromethyl, chloromethyl, dichloromethyl, trichloromethyl, bromomethyl, dibromomethyl, tribromomethyl, difluoroethyl, trichloroethyl, dichlorodifluoroethyl, pentafluoroethyl, heptafluoropropyl, nonafluorobutyl, decafluoropentyl, tridecafluorohexyl, pentadecafluoroheptyl, heptadecafluorooctyl, cyanomethyl, hydroxylmethyl, 1-hydroxyethyl, 2-hydroxyethyl, 3-hydroxypropyl, 3-hydroxybutyl, 4-hydroxybutyl, and 1,2-dihydroxyethyl.

Examples of the optionally substituted C6-C20 aryl group represented by $R^1$ through $R^{10}$ and $R^{18}$ in formula (I) include phenyl, naphthyl, 2-methylphenyl, 3-methylphenyl, 4-methylphenyl, 4-vinylphenyl, 3-isopropylphenyl, 4-isopropylphenyl, 4-butylphenyl, 4-isobutylphenyl, 4-t-butylphenyl, 4-hexylphenyl, 4-cyclohexylphenyl, 4-octylphenyl, 4-(2-ethylhexyl)phenyl, 4-stearylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4-di-t-butylphenyl, cyclohexylphenyl, and hydroxyphenyl.

Examples of the optionally substituted C7-C20 arylalkyl group represented by $R^1$ through $R^{10}$ and $R^{18}$ in formula (I) include benzyl, phenethyl, phenacyl, 2-phenylpropan-2-yl, diphenylmethyl, triphenylmethyl, styryl, cinnamyl, 2-hydroxybenzyl, 3-hydroxybenzyl, 4-hydroxybenzyl, 2-hydroxyphenethyl, 3-hydroxyphenethyl, 4-hydroxyphenethyl, 2-hydroxyphenacyl, 3-hydroxyphenacyl, 4-hydroxyphenacyl, 2-phenoxyethyl, and 2-phenylthioethyl.

The methylene chain in the alkyl, aryl, and arylalkyl groups may be interrupted by —O—, —S—, —CO—, —CO—O—, or —O—CO—. Examples of such interrupted groups include optionally substituted C1-C18 alkoxy, optionally substituted C6-C20 aryloxy, optionally substituted C1-C18 thioalkoxy, optionally substituted C6-C20 thiophenoxy, and optionally substituted C1-C12 ester groups.

Examples of the optionally substituted C1-C18 alkoxy include methoxy, ethoxy, propoxy, isopropoxy, butoxy, s-butoxy, t-butoxy, isobutoxy, pentyloxy, isoamyloxy, t-amyloxy, hexyloxy, cyclohexyloxy, cyclohexylmethyloxy, tetrahydrofuranyloxy, tetrahydropyranyloxy, hydroxymethyloxy, 1-hydroxyethyloxy, 2-hydroxyethyloxy, 3-hydroxypropyloxy, 2-hydroxypropyloxy, 2,3-dihydroxypropyloxy, 2-hydroxy-1-methylethyloxy, 2-hydroxybutyloxy, 4-hydroxybutyloxy, 2,3-dihydroxybutyloxy, 3,4-dihydroxybutyloxy, 2,3,4-trihydroxybutyloxy, 2-(2-hydroxyethyloxy)ethyloxy, 2-hydroxy-3-methoxypropyloxy, 5-hydroxypentyloxy, 2-hydroxy-2-(hydroxymethyl)butyloxy, 3-hydroxy-2-di(hydroxymethyl)propyloxy, 6-hydroxyhexyloxy, 5,6-dihydroxyhexyloxy, 2-hydroxycyclohexyloxy, 4-hydroxycyclohexyloxy, 2,3,4,5,6-pentahydroxycyclohexyloxy, 2-(2-(2-hydroxyethyloxy)ethyloxy)ethyloxy, 4-hydroxymethylcyclohexylmethyloxy, and 2-di(hydroxymethyl)butyloxy.

Examples of the optionally substituted C6-C20 aryloxy are phenoxy and hydroxyphenyloxy.

Examples of the optionally substituted C1-C18 thioalkoxy include methylthio, ethylthio, propylthio, isopropylthio, butylthio, s-butylthio, t-butylthio, isobutylthio, amylthio, isoamylthio, t-amylthio, hexylthio, cyclohexylthio, adamantylthio, 2-hydroxyethylthio, 3-hydroxypropylthio, 2,3-dihydroxypropylthio, and 2-hydroxy-1-methylpropylthio.

Examples of the optionally substituted C6-C20 thiophenoxy are phenylthio and hydroxyphenylthio.

Examples of the optionally substituted C1-C12 ester group include methoxycarbonyl, ethoxycarbonyl, isopropyloxycarbonyl, phenoxycarbonyl, acetoxy, methoxyacetyloxy, propionyloxy, butyryloxy, t-butylcarbonyloxy, benzoyloxy, adamantylcarbonyloxy, 2-hydroxyethoxycarbonyl, 3-hydroxypropyloxycarbonyl, 4-hydroxyphenoxycarbonyl, 3-hydroxypropionyloxy, 4-hydroxybutyryloxy, and 4-hydroxybenzoyloxy.

The C1-C18 alkyl represented by $R^1$ to $R^{18}$ in formula (I), the C1-C18 alkoxy represented by $R^1$ to $R^{18}$ in formula (I), the C1-C18 thioalkoxy represented by $R^1$ to $R^{18}$ in formula (I), the C1-C12 ester group represented by $R^1$ to $R^{18}$ in formula (I), the C6-C20 aryl represented by $R^1$ to $R^{10}$ and $R^{18}$ in formula (I), the C7-C20 arylalkyl represented by $R^1$ to $R^{10}$ and $R^{18}$ in formula (I), C6-C20 aryloxy represented by $R^1$ to $R^{10}$ and $R^{18}$ in formula (I), and the C6-C20 thiophenoxy represented by $R^1$ to $R^{10}$ and $R^{18}$ in formula (I) may have a substituent.

Examples of the substituent include alkyl, such as methyl, ethyl, propyl, isopropyl, butyl, isobutyl, t-butyl, pentyl, isopentyl, t-pentyl, neopentyl, hexyl, isohexyl, heptyl, octyl, 2-ethylhexyl, nonyl, decyl, undecyl, dodecyl, tridecyl, isotridecyl, myristyl, palmityl, stearyl, cyclopropyl, cyclohexyl, 1-adamantyl, 2-adamantyl, 2-methyl-1-adamantyl, 2-methyl-2-adamantyl, 2-ethyl-1-adamantyl, 2-ethyl-2-adamantyl, 2-norbornyl, 2-norbornylmethyl, camphor-10-yl vinyl, allyl, isopropenyl, 1-propenyl, 2-methoxy-1-propenyl, fluoromethyl, difluoromethyl, trifluoromethyl, chloromethyl, dichloromethyl, trichloromethyl, bromomethyl, dibromomethyl, tribromomethyl, difluoroethyl, trichloroethyl, dichlorodifluoroethyl, pentafluoroethyl, heptafluoropropyl, nonafluorobutyl, decafluoropentyl, tridecafluorohexyl, pentadecafluoroheptyl, heptadecafluorooctyl, methoxymethyl, methoxyethoxymethyl, methylthiomethyl, ethoxyethyl, butoxymethyl, t-butylthiomethyl, 4-pentenyloxymethyl, trichloroethoxymethyl, bis(2-chloroethoxy)methyl, methoxycyclohexyl, 1-(2-chloroethoxy)ethyl, methoxyethyl, 1-methyl-1-methoxyethyl, ethyldithioethyl, trimethylsilylethyl, t-butyldimethylsilyloxymethyl, 2-(trimethylsilyl)ethoxymethyl, t-butoxycarbonylmethyl, ethyloxycarbonylmethyl, ethylcarbonylmethyl, t-butoxycarbonylmethyl, acryloyloxyethyl, methacryloyloxyethyl, 2-methyl-2-adamantyloxycarbonylmethyl, and acetylethyl; aryl, such as phenyl, 1-naphthyl, 2-naphthyl, anthracen-1-yl, phenanthren-1-yl, o-tolyl, m-tolyl, p-tolyl, 4-vinylphenyl, ethylphenyl, propylphenyl, 3-isopropylphenyl, 4-isopropylphenyl, 4-butylphenyl, 4-isobutylphenyl, 4-t-butylphenyl, 4-hexylphenyl, 4-cyclohexylphenyl, 4-octylphenyl, 4-(2-ethylhexyl)phenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4-di-t-butylphenyl, 2,5-di-t-butylphenyl, 2,6-di-t-butylphenyl, 2,4-di-t-pentylphenyl, 2,5-di-t-amylphenyl, cyclohexylphenyl, biphenylyl, 2,4,5-trimethylphenyl, 9-fluorenyl, 4-chlorophenyl, 3,4-dichlorophenyl, 4-trichlorophenyl, 4-trifluorophenyl, fluorophenyl, trifluoromethylphenyl, pentafluorophenyl, heptafluoro-p-tolyl, 4-formylphenyl, 4-nitrophenyl, ethoxynaphthyl, 4-fluoromethylphenyl, 4-methoxyphenyl, and 2,4-dinitrophenyl; arylalkyl, such as benzyl, methylbenzyl, dimethylbenzyl, trimethylbenzyl, phenylbenzyl, diphenylmethyl, triphenylmethyl, 2-phenylethyl, 2-phenylpropyl, styryl, cinnamyl, fluorobenzyl, chlorobenzoyl, bromobenzyl, cyanobenzyl, dichlorobenzyl, methoxybenzyl, dimethoxybenzyl, benzyloxymethyl, methoxybenzyloxymethyl, 1-methyl-1-benzyloxyethyl, 1-methyl-1-benzyloxy-2-fluoroethyl, guaiacolmethyl, phenoxymethyl, phenylthiomethyl, nitrobenzyl, dinitrobenzhydryl, dibenzosuberyl, (phenyldimethylsilyl)methoxymethyl, phenylsulfonylethyl, triphenylphosphonioethyl, triphenylmethoxymethyl, phenacyl, and bromophenacyl; alkoxy represented by RO—, acyl represented by RCO—, ester group represented by RCOO— or ROCO—, carbonate represented by ROCOO—, sulfanyl represented by RS—, sulfinyl represented by RSO—, sulfonyl represented by $RSO_2$—, and sulfonic ester group represented by $RSO_3$—, wherein R represents the alkyl, aryl, or arylalkyl group described or a heterocyclic group, such as tetrahydropyranyl, 3-bromotetrahydropyranyl, tetrahydrothiopyranyl, methoxytetrahydropyranyl, methoxytetrahydrothiopyranyl, 4-methoxytetrahydrothiopyran-S,S-dioxide-4-yl, 1-[(2-chloro-4-methyl)phenyl]-4-methoxypiperidin-4-yl, 1,4-dioxan-2-yl, tetrahydrofuranyl, tetrahydrothiofuranyl, 2,3,3a,4,5,6,7,7a-octahydro-7,8,8-trimethyl-4,7-metanobenzofuran-2-yl, 2-pyridylmethyl, 4-pyridylmethyl, 3-picolin-N-oxide-2-ylmethyl, 1,3-benzodithioranyl, benzisothiazolin-S,S-dioxide-3-yl, and tetrafluoro-4-pyridyl; formyl; carboxyl; formyloxy; sulfo; silyloxy, such as trimethylsilyloxy, triethylsilyloxy, tripropylsilyloxy, dimethylpropylsilyloxy, diethylpropylsilyloxy, dimethyl(1,1,2,2-tetramethyl)ethylsilyloxy, butyldimethylsilyloxy, butyldiphenylsilyloxy, tribenzylsilyloxy, trixylylsilyloxy, triphenylsilyloxy, diphenylmethylsilyloxy, and butylmethoxyphenylsilyloxy; phosphoric ester group; benzylthiocarbonate; methyldithiocarbonate; hydroxyl; nitro; and halogen, such as fluorine, chlorine, bromine, or iodine.

Examples of the anion represented by $X_1^-$ in formula (I) include halide anions, such as chloride, bromide, iodide, and fluoride; inorganic anions, such as perchlorate, chlorate, thiocyanate, hexafluorophosphate, hexafluoroantimonate, hexafluoroarsenate, and tetrafluoroborate; organic sulfonate anions, such as methanesulfonate, fluorosulfonate, benzenesulfonate, toluenesulfonate, 1-naphthylsulfonate, 2-naphthylsulfonate, trifluoromethanesulfonate, pentafluoroethanesulfonate, heptafluoropropanesulfonate, nonafluorobutanesulfonate, undecafluoropentanesulfonate, tridecafluorohexanesulfonate, pentadecafluoroheptanesulfonate, heptadecafluorooctanesulfonate, perfluoro-4-ethylcyclohexanesulfonate, N-alkyl(or aryl)diphenylamine-4-sulfonate, 2-amino-4-methyl-5-chlorobenzenesulfonate, 2-amino-5-nitrobenenesulfonate, the sulfonate described in JP 2004-53799A, camphorsulfonate, fluorobenzenesulfonate, difluorobenzenesulfonate, trifluorobenzenesulfonate, tetrafluorobenzenesulfonate, and pentafluorobenzenesulfonate; organic phosphate anions, such as octylphosphate, dodecylphosphate, octadecylphosphate, phenylphosphate, nonylphenylphosphate, and 2,2'-methylenebis(4,6-di-t-butylphenyl)phosphonate; organic fluorosulfonimide ions, such as bis(trifluoromethanesulfone)imide ion, bis(pentafluoroethanesulfone)imide ion, bis(heptafluoropropanesulfone)imide ion, bis(nonafluorobutanesulfone)imide ion, bis(undecafluoropentanesulfone)imide ion, bis(pentadecafluoroheptanesulfone)imide ion, bis(tridecafluorohexanesulfone)imide ion bis(heptadecafluorooctanesulfonimide) ion, (trifluoromethanesulfone)(nonafluorobutanesulfone)imide ion, (methanesulfone)(trifluoromethanesulfone)imide ion, and cyclohexafluoropropane-1,3-bis(sulfonyl)imide ion; tetraarylborate anions, such as tetrakis(pentafluorophenyl)borate ion, tetrakis(4-fluorophenyl)borate ion, tetraphenylborate ion, the borate ions described in JP 2007-112854A, JP 6-184170A, JP 2002-526391A, and JP 2007-285538A; various aliphatic or aromatic carboxylate anions; and organic sulfonylmethide ions, such as tris(trifluoromethanesulfonyl)methide and tris(methanesulfonyl)methide. Also included are alkylsulfonate ions, fluoro-substituted alkylsulfonate ions, and alkylsulfonimides or fluoro-substituted alkylsulfonimides substituted with acryloyloxy, methacryloyloxy, or aliphatic cycloalkyl, such as norbornyl or adamantyl. If desired, a quencher anion capable of deexciting (quenching) an active molecule in an excited state or a metallocene compound anion of, for example, a ferrocene or ruthenocene compound having an anionic group (e.g., a carboxyl group, a phosphonic acid group, or a sulfonic acid group) on its cyclopentadienyl ring may be used. Of these anions preferred are organic sulfonate anions in view of safety and reactivity (in both deprotection reaction and crosslinking reaction).

Preferred of the compounds of formula (I) are those represented by general formula (II) below for their high solubility in a solvent and high developing properties as a photo-acid generator.

[Chem. 2]

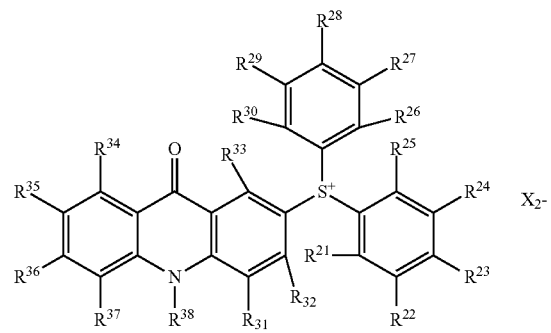

(II)

wherein $R^{21}$, $R^{22}$, $R^{23}$, $R^{24}$, $R^{25}$, $R^{26}$, $R^{27}$, $R^{28}$, $R^{29}$, and $R^{30}$ each independently represent a hydrogen atom, a halogen atom, a hydroxyl group, a nitro group, an optionally substituted alkyl group having 1 to 18 carbon atoms, an optionally substituted aryl group having 6 to 20 carbon atoms, or an optionally substituted arylalkyl group having 7 to 20 carbon atoms;

$R^{31}$, $R^{32}$, $R^{33}$, $R^{34}$, $R^{35}$, $R^{36}$, and $R^{37}$ each independently represent a hydrogen atom, a halogen atom, a hydroxyl group, a nitro group, or an optionally substituted alkyl group having 1 to 18 carbon atoms;

$R^{38}$ represents an unsubstituted alkyl group having 1 to 10 carbon atoms;

the number of optional substituents when present on the C1-C18 alkyl group represented by $R^{21}$ through $R^{38}$, the C6-C20 aryl group represented by $R^{21}$ through $R^{30}$, and the C7-C20 arylalkyl group represented by $R^{21}$ through $R^{30}$ being not limited;

the methylene chain of the C1-C18 alkyl group represented by $R^{21}$ through $R^{38}$, the C6-C20 aryl group represented by $R^{21}$ through $R^{30}$, and the C7-C20 arylalkyl group represented by $R^{21}$ through $R^{30}$ being optionally interrupted by —O—, —S—, —CO—, —CO—O—, or —O—CO—; and $X_2^-$ represents a monovalent anion;

provided that at least one of $R^{21}$ through $R^{30}$ is a hydroxyl group, a hydroxyl-substituted thioalkoxy group having 1 to 18 carbon atoms, or a hydroxyl-substituted thiophenoxy group.

Examples of the halogen represented by $R^{21}$ to $R^{37}$ in formula (II) include fluorine, chlorine, bromine, and iodine.

Examples of the optionally substituted C1-C18 alkyl represented by $R^{21}$ to $R^{37}$ in formula (II), and the unsubstituted C1-C10 alkyl group represented by $R^{38}$ in formula (II) include methyl, ethyl, propyl, isopropyl, butyl, s-butyl, t-butyl, isobutyl, amyl, isoamyl, t-amyl, hexyl, cyclohexyl, isohexyl, 2-ethylhexyl, heptyl, octyl, nonyl, decyl, undecyl, dodecyl, tridecyl, isotridecyl, tetradecyl, hexadecyl, heptadecyl, octadecyl, 1-adamantyl, 2-adamantyl, 2-methyl-1-adamantyl, 2-methyl-2-adamantyl, 2-ethyl-1-adamantyl, 2-ethyl-2-adamantyl, 2-norbornyl, 2-norbornylmethyl, vinyl, allyl, isopropenyl, 1-propenyl, fluoromethyl, difluoromethyl, trifluoromethyl, chloromethyl, dichloromethyl, trichloromethyl, bromomethyl, dibromomethyl, tribromomethyl, difluoroethyl, trichloroethyl, dichlorodifluoroethyl, pentafluoroethyl, heptafluoropropyl, nonafluorobutyl, decafluoropentyl, tridecafluorohexyl, pentadecafluoroheptyl, heptadecafluorooctyl, cyanomethyl, hydroxylmethyl, 1-hydroxyethyl, 2-hydroxyethyl, 3-hydroxypropyl, 3-hydroxybutyl, 4-hydroxybutyl, and 1,2-dihydroxyethyl.

Examples of the optionally substituted C6-C20 aryl group represented by $R^{21}$ through $R^{30}$ in formula (II) include phenyl, naphthyl, 2-methylphenyl, 3-methylphenyl, 4-methylphenyl, 4-vinylphenyl, 3-isopropylphenyl, 4-isopropylphenyl, 4-butylphenyl, 4-isobutylphenyl, 4-t-butylphenyl, 4-hexylphenyl, 4-cyclohexylphenyl, 4-octylphenyl, 4-(2-ethylhexyl)phenyl, 4-stearylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4-di-t-butylphenyl, cyclohexylphenyl, and hydroxyphenyl.

Examples of the optionally substituted C7-C20 arylalkyl group represented by $R^{21}$ through $R^{30}$ in formula (II) include benzyl, phenethyl, phenacyl, 2-phenylpropan-2-yl, diphenylmethyl, triphenylmethyl, styryl, cinnamyl, 2-hydroxybenzyl, 3-hydroxybenzyl, 4-hydroxybenzyl, 2-hydroxyphenethyl, 3-hydroxyphenethyl, 4-hydroxyphenethyl, 2-hydroxyphenacyl, 3-hydroxyphenacyl, 4-hydroxyphenacyl, 2-phenoxyethyl, and 2-phenylthioethyl.

The methylene chain in the alkyl, aryl, and arylalkyl groups may be interrupted by —O—, —S—, —CO—, —CO—O—, or —O—CO—. Examples of such interrupted groups include optionally substituted C1-C18 alkoxy, optionally substituted C6-C20 aryloxy, optionally substituted C1-C18 thioalkoxy, optionally substituted C6-C20 thiophenoxy, and optionally substituted C1-C12 ester groups.

Examples of the optionally substituted C1-C18 alkoxy include methoxy, ethoxy, propoxy, isopropoxy, butoxy, s-butoxy, t-butoxy, isobutoxy, pentyloxy, isoamyloxy, t-amyloxy, hexyloxy, cyclohexyloxy, cyclohexylmethyloxy, tetrahydrofuranyloxy, tetrahydropyranyloxy, hydroxymethyloxy, 1-hydroxyethyloxy, 2-hydroxyethyloxy, 3-hydroxypropyloxy, 2-hydroxypropyloxy, 2,3-dihydroxypropyloxy, 2-hydroxy-1-methylethyloxy, 2-hydroxybutyloxy, 4-hydroxybutyloxy, 2,3-dihydroxybutyloxy, 3,4-dihydroxybutyloxy, 2,3,4-trihydroxybutyloxy, 2-(2-hydroxyethyloxy)ethyloxy, 2-hydroxy-3-methoxypropyloxy, 5-hydroxypentyloxy, 2-hydroxy-2-(hydroxymethyl)butyloxy, 3-hydroxy-2-di(hydroxymethyl) propyloxy, 6-hydroxyhexyloxy, 5,6-dihydroxyhexyloxy, 2-hydroxycyclohexyloxy, 4-hydroxycyclohexyloxy, 2,3,4,5,6-pentahydroxycyclohexyloxy, 2-(2-(2-hydroxyethyloxy) ethyloxy)ethyloxy, 4-hydroxymethylcyclohexylmethyloxy, and 2-di(hydroxymethyl)butyloxy.

Examples of the optionally substituted C6-C20 aryloxy are phenoxy and hydroxyphenyloxy.

Examples of the optionally substituted C1-C18 thioalkoxy include methylthio, ethylthio, propylthio, isopropylthio, butylthio, s-butylthio, t-butylthio, isobutylthio, amylthio, isoamylthio, t-amylthio, hexylthio, cyclohexylthio, adamantylthio, 2-hydroxyethylthio, 3-hydroxypropylthio, 2,3-dihydroxypropylthio, and 2-hydroxy-1-methylpropylthio.

Examples of the optionally substituted C6-C20 thiophenoxy are phenylthio and hydroxyphenylthio.

Examples of the optionally substituted C1-C12 ester group include methoxycarbonyl, ethoxycarbonyl, isopropyloxycarbonyl, phenoxycarbonyl, acetoxy, methoxyacetyloxy, propionyloxy, butyryloxy, t-butylcarbonyloxy, benzoyloxy, adamantylcarbonyloxy, 2-hydroxyethoxycarbonyl, 3-hydroxypropyloxycarbonyl, 4-hydroxyphenoxycarbonyl, 3-hydroxypropionyloxy, 4-hydroxybutyryloxy, and 4-hydroxybenzoyloxy.

The C1-C18 alkyl represented by $R^{21}$ to $R^{37}$ in formula (II), the C1-C18 alkoxy represented by $R^{21}$ to $R^{37}$ in formula (II), the C1-C18 thioalkoxy represented by $R^{21}$ to $R^{37}$ in formula (II), the C1-C12 ester group represented by $R^{21}$ to $R^{37}$ in formula (II), the C6-20 aryl represented by $R^{21}$ to $R^{30}$ in formula (II), the C7-C20 arylalkyl represented by $R^{21}$ to $R^{30}$ in formula (II), C6-C20 aryloxy represented by $R^{21}$ to $R^{30}$ in formula (II), and the C6-C20 thiophenoxy represented by $R^{21}$ to $R^{30}$ in formula (II) may have a substituent.

Examples of the substituent include alkyl, such as methyl, ethyl, propyl, isopropyl, butyl, isobutyl, t-butyl, pentyl, isopentyl, t-pentyl, neopentyl, hexyl, isohexyl, heptyl, octyl, 2-ethylhexyl, nonyl, decyl, undecyl, dodecyl, tridecyl, isotridecyl, myristyl, palmityl, stearyl, cyclopropyl, cyclohexyl, 1-adamantyl, 2-adamantyl, 2-methyl-1-adamantyl, 2-methyl-2-adamantyl, 2-ethyl-1-adamantyl, 2-ethyl-2-adamantyl, 2-norbornyl, 2-norbornylmethyl, camphor-10-yl vinyl, allyl, isopropenyl, 1-propenyl, 2-methoxy-1-propenyl, fluoromethyl, difluoromethyl, trifluoromethyl, chloromethyl, dichloromethyl, trichloromethyl, bromomethyl, dibromomethyl, tribromomethyl, difluoromethyl, trichloroethyl, dichlorodifluoroethyl, pentafluoroethyl, heptafluoropropyl, nonafluorobutyl, decafluoropentyl, tridecafluorohexyl, pentadecafluoroheptyl, heptadecafluorooctyl, methoxymethyl, methoxyethoxymethyl, methylthiomethyl, ethoxyethyl, butoxymethyl, t-butylthiomethyl, 4-pentenyloxymethyl, trichloroethoxymethyl, bis(2-chloroethoxy)methyl, methoxycyclohexyl, 1-(2-chloroethoxy)ethyl, methoxyethyl, 1-methyl-1-methoxyethyl, ethyldithioethyl, trimethylsilylethyl, t-butyldimethylsilyloxymethyl, 2-(trimethylsilyl) ethoxymethyl, t-butoxycarbonylmethyl, ethyloxycarbonylmethyl, ethylcarbonylmethyl, t-butoxycarbonylmethyl, acryloyloxyethyl, methacryloyloxyethyl, 2-methyl-2-adamantyloxycarbonylmethyl, and acetylethyl; aryl, such as phenyl, 1-naphthyl, 2-naphthyl, anthracen-1-yl, phenanthren-1-yl, o-tolyl, m-tolyl, p-tolyl, 4-vinylphenyl, ethylphenyl, propylphenyl, 3-isopropylphenyl, 4-isopropylphenyl, 4-butylphenyl, 4-isobutylphenyl, 4-t-butylphenyl, 4-hexylphenyl, 4-cyclohexylphenyl, 4-octylphenyl, 4-(2-ethylhexyl)phenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4-di-t-butylphenyl, 2,5-di-t-butylphenyl, 2,6-di-t-butylphenyl, 2,4-di-t-pentylphenyl, 2,5-di-t- amylphenyl, cyclohexylphenyl, biphenylyl, 2,4,5-trimethylphenyl, 9-fluorenyl, 4-chlorophenyl, 3,4-dichlorophenyl, 4-trichlorophenyl, 4-trifluorophenyl, fluorophenyl, trifluoromethylphenyl, pentafluorophenyl, heptafluoro-p-tolyl, 4-formylphenyl, 4-nitrophenyl, ethoxynaphthyl, 4-fluoromethylphenyl, 4-methoxyphenyl, and 2,4-dinitrophenyl; aryalkyl, such as benzyl, methylbenzyl, dimethylbenzyl, trimethylbenzyl, phenylbenzyl, diphenylmethyl, triphenylmethyl, 2-phenylethyl, 2-phenylpropyl, styryl, cinnamyl, fluorobenzyl, chlorobenzoyl, bromobenzyl, cyanobenzyl, dichlorobenzyl, methoxybenzyl, dimethoxybenzyl, benzyloxymethyl, methoxybenzyloxymethyl, 1-methyl-1-benzyloxyethyl, 1-methyl-1-benzyloxy-2-fluoroethyl, guaiacolmethyl, phenoxymethyl, phenylthiomethyl, nitrobenzyl, dinitrobenzhydryl, dibenzosuberyl, (phenyldimethylsilyl)methoxymethyl, phenylsulfonylethyl, triphenylphosphonioethyl, triphenylmethoxymethyl, phenacyl, and bromophenacyl; alkoxy represented by RO—, acyl represented by RCO—, ester group represented by RCOO— or ROCO—, carbonate represented by ROCOO—, sulfanyl represented by RS—, sulfinyl represented by RSO—, sulfonyl represented by $RSO_2$—, and sulfonic ester group represented by $RSO_3$—, wherein R represents the alkyl, aryl, or arylalkyl group described or a heterocyclic group, such as tetrahydropyranyl, 3-bromotetrahydropyranyl, tetrahydrothiopyranyl, methoxytetrahydropyranyl, methoxytetrahydrothiopyranyl, 4-methoxytetrahydrothiopyran-S,S-dioxide-4-yl, 1-[(2-chloro-4-methyl)phenyl]-4-methoxypiperidin-4-yl, 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 2-pyridylmethyl, 4-pyridylmethyl, 3-picolin-N-oxide-2-yl-methyl, 1,3-benzodithioranyl, benzisothiazolin-S,S-dioxide-3-yl, and tetrafluoro-4-pyridyl; formyl; carboxyl; formyloxy; sulfo; silyloxy, such as trimethylsilyloxy, triethylsilyloxy, tripropylsilyloxy, dimethylpropylsilyloxy, diethylpropylsilyloxy, dimethyl(1,1,2,2-tetramethyl)ethylsilyloxy, butyldimethylsilyloxy, butyldiphenylsilyloxy, tribenzylsilyloxy, trixylylsilyloxy, triphenylsilyloxy, diphenylmethylsilyloxy, and butylmethoxyphenylsilyloxy; phosphoric ester group; benzylthiocarbonate; methyldithiocarbonate; hydroxyl; nitro; and halogen, such as fluorine, chlorine, bromine, or iodine.

Examples of the anion represented by $X_2^-$ in formula (II) include halide anions, such as chloride, bromide, iodide, and fluoride; inorganic anions, such as perchlorate, chlorate, thiocyanate, hexafluorophosphate, hexafluoroantimonate, hexafluoroarsenate, and tetrafluoroborate; organic sulfonate anions, such as methanesulfonate, fluorosulfonate, benzenesulfonate, toluenesulfonate, 1-naphthylsulfonate, 2-naphthylsulfonate, trifluoromethanesulfonate, pentafluoroethanesulfonate, heptafluoropropanesulfonate, nonafluorobutanesulfonate, undecafluoropentanesulfonate, tridecafluorohexanesulfonate, pentadecafluoroheptanesulfonate, heptadecafluorooctanesulfonate, perfluoro-4-ethylcyclohexanesulfonate, N-alkyl (or aryl)diphenylamine-4-sulfonate, 2-amino-4-methyl-5-chlorobenzenesulfonate, 2-amino-5-nitrobenenesulfonate, the sulfonate described in JP 2004-53799A, camphorsulfonate, fluorobenzenesulfonate, difluorobenzenesulfonate, trifluorobenzenesulfonate, tetrafluorobenzenesulfonate, and pentafluorobenzenesulfonate; organic phosphonate anions, such as octylphosphonate, dodecylphosphonate, octadecylphosphonate, phenylphosphonate, nonylphenylphosphonate, and 2,2'-methylenebis(4,6-di-t-butylphenyl)phosphonate; organic fluorosulfonimide ions, such as bis(trifluoromethanesulfone)imide ion, bis(pentafluoroethanesulfone)imide ion, bis(heptafluoropropanesulfone)imide ion, bis(nonafluorobutanesulfone)imide ion, bis(undecafluoropentanesulfone)imide ion, bis(pentadecafluoroheptanesulfone)imide ion, bis(tridecafluorohexanesulfone)imide ion bis(heptadecafluorooctanesulfonimide) ion, (trifluoromethanesulfone)(nonafluorobutanesulfone)imide ion, (methanesulfone) (trifluoromethanesulfone)imide ion, and cyclohexafluoropropane-1,3-bis(sulfonyl)imide ion; tetraarylborate anions, such as tetrakis(pentafluorophenyl)borate anion, tetrakis(4-fluorophenyl)borate ion, tetraphenylborate ion, the borate ions described in JP 2007-112854A, JP 6-184170A, JP 2002-526391A, and JP 2007-285538A; various aliphatic or aromatic carboxylate anions; and organic sulfonylmethide ions, such as tris(trifluoromethanesulfonyl)methide and tris(methanesulfonyl)methide. Also included are alkylsulfonate ions, fluoro-substituted alkylsulfonate ions, and alkylsulfonimides or fluoro-substituted alkylsulfonimides substituted with acryloyloxy, methacryloyloxy, or aliphatic cycloalkyl, such as norbornyl or adamantyl. If desired, a quencher anion capable of deexciting (quenching) an active molecule in an excited state or a metallocene compound anion of, for example, a ferrocene or ruthenocene compound having an anionic group (e.g., a carboxyl group, a phosphonic acid group, or a sulfonic acid group) on its cyclopentadienyl ring may be used. Of these anions preferred are organic sulfonate anions in view of safety and reactivity (in both deprotection reaction and crosslinking reaction).

Specific examples of the cation of the aromatic sulfonium salt compound represented by formula (II) include the following cations numbered from 1 through 16:

[Chem. 3]

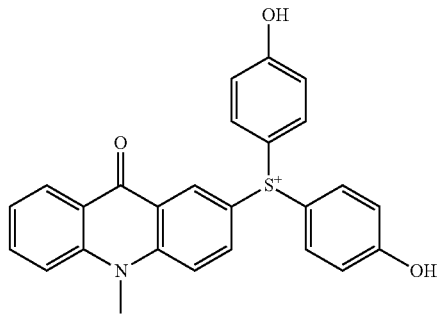

No.1

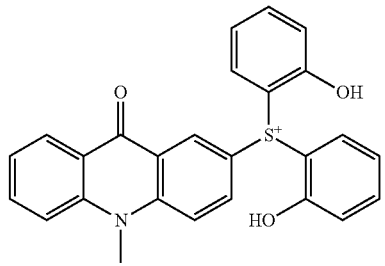

No.2

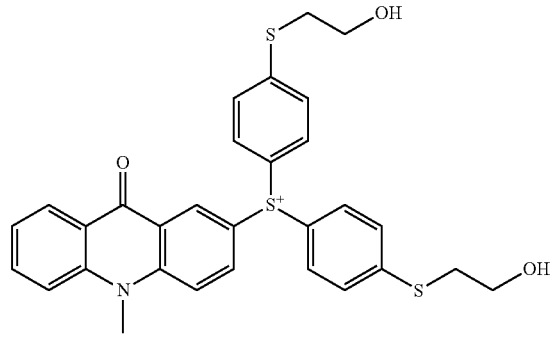

No.3

No.4
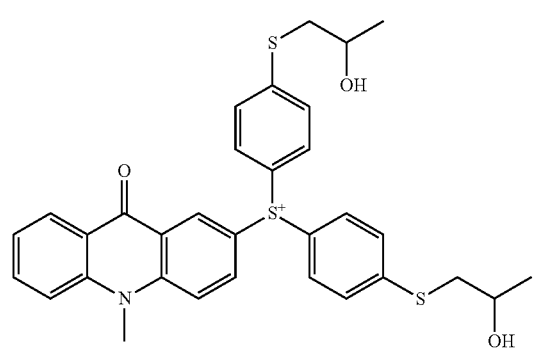
No.5
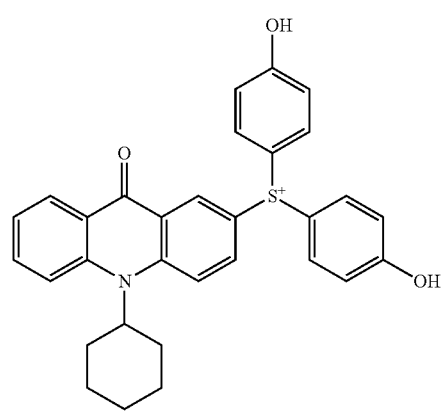
No.6
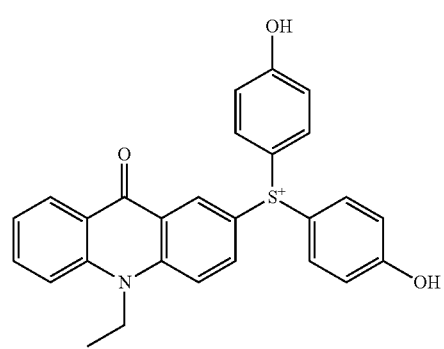
No.7
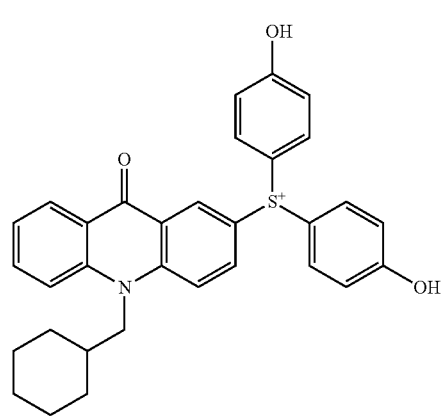
No.8
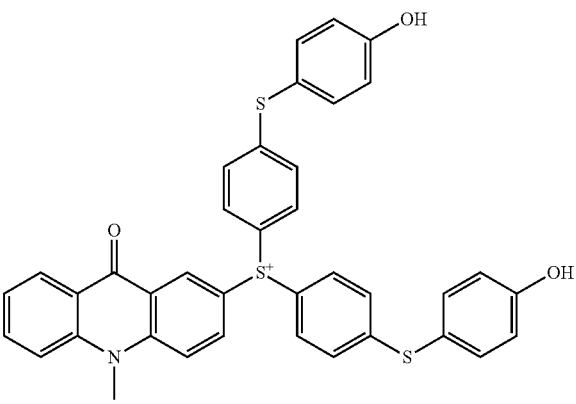
No.9
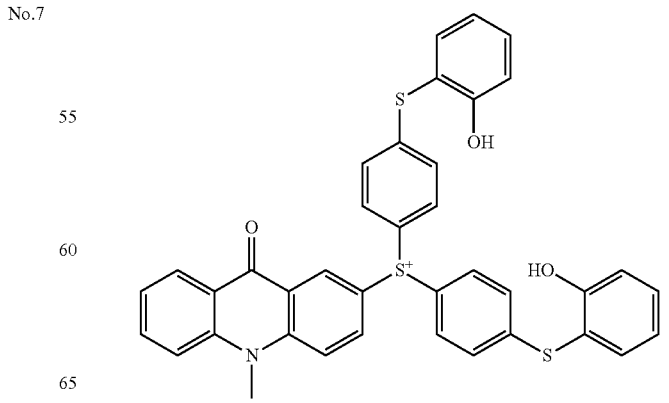
No.10

[Chem. 4]

No. 11
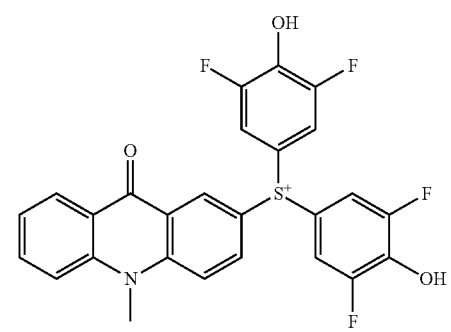

No. 12
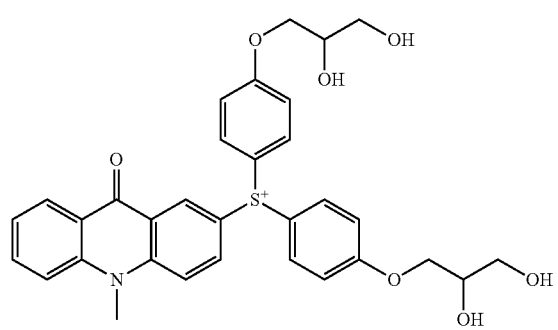

No. 13
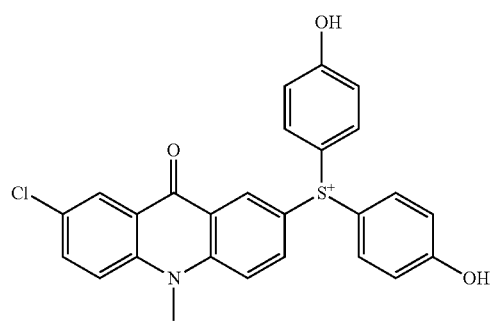

No. 14
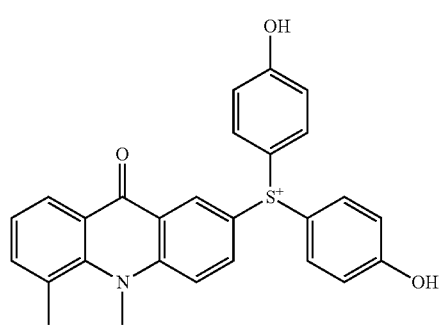

No. 15
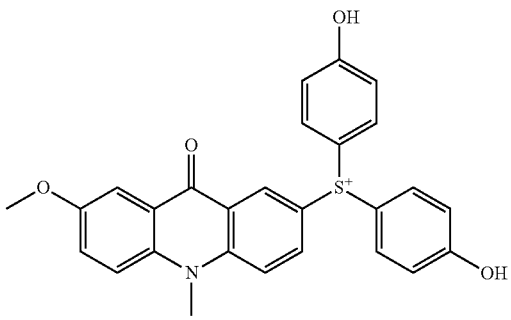

No. 16
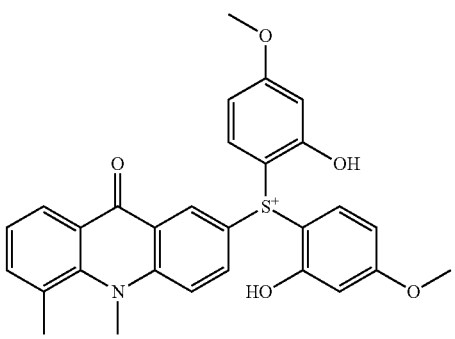

Of the compounds represented by formula (I), those represented by general formula (III) below are preferred to provide a cationic polymerization initiator exhibiting high curing properties.

[Chem. 5]

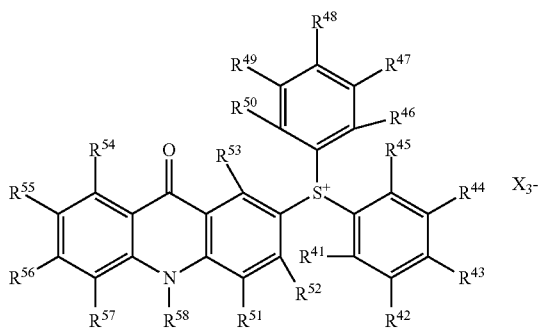

(III)

wherein $R^{41}$, $R^{42}$, $R^{43}$, $R^{44}$, $R^{45}$, $R^{46}$, $R^{47}$, $R^{48}$, $R^{49}$, and $R^{50}$ each independently represent a hydrogen atom, a halogen atom, a hydroxyl group, a nitro group, an optionally substituted alkyl group having 1 to 18 carbon atoms, an optionally substituted aryl group having 6 to 20 carbon atoms, or an optionally substituted arylalkyl group having 7 to 20 carbon atoms;

$R^{51}$, $R^{52}$, $R^{53}$, $R^{54}$, $R^{55}$, $R^{56}$, and $R^{57}$ each independently represent a hydrogen atom, a halogen atom, a hydroxyl group, a nitro group, or an optionally substituted alkyl group having 1 to 18 carbon atoms;

$R^{58}$ represents a hydrogen atom, a substituted alkyl group having 1 to 10 carbon atoms, an optionally substituted alkyl group having 11 to 18 carbon atoms, an optionally substituted aryl group having 6 to 20 carbon atoms, or an optionally substituted arylalkyl group having 7 to 20 carbon atoms;

the number of optional substituents when present on the C1-C18 alkyl group represented by $R^{41}$ through $R^{58}$, the C6-C20 aryl group represented by $R^{41}$ through $R^{50}$ and $R^{58}$, and the C7-C20 arylalkyl group represented by $R^{41}$ through $R^{50}$ and $R^{58}$ being not limited;

the methylene chain of the C1-C18 alkyl group represented by $R^{41}$ through $R^{58}$, the C6-C20 aryl group represented by $R^{41}$ through $R^{41}$ and $R^{50}$, and the C7-C20 arylalkyl group represented by $R^{41}$ through $R^{50}$ and $R^{58}$ being optionally interrupted by —O—, —S—, —CO—, —CO—O—, or —O—CO—; and $X_3^-$ represents a monovalent anion.

Examples of the halogen represented by $R^{41}$ to $R^{57}$ in formula (III) include fluorine, chlorine, bromine, and iodine.

Examples of the optionally substituted C1-C18 alkyl represented by $R^{41}$ to $R^{57}$, the C1-C10 substituted alkyl represented by $R^{58}$, and the optionally substituted C11-C18 alkyl represented by $R^{58}$ in formula (III) include methyl, ethyl, propyl, isopropyl, butyl, s-butyl, t-butyl, isobutyl, amyl, isoamyl, t-amyl, hexyl, cyclohexyl, isohexyl, 2-ethylhexyl, heptyl, octyl, nonyl, decyl, undecyl, dodecyl, tridecyl, isotridecyl, tetradecyl, hexadecyl, heptadecyl, octadecyl, 1-adamantyl, 2-adamantyl, 2-methyl-1-adamantyl, 2-methyl-2-adamantyl, 2-ethyl-1-adamantyl, 2-ethyl-2-adamantyl, 2-norbornyl, 2-norbornylmethyl, vinyl, allyl, isopropenyl, 1-propenyl, fluoromethyl, difluoromethyl, trifluoromethyl, chloromethyl, dichloromethyl, trichloromethyl, bromomethyl, dibromomethyl, tribromomethyl, difluoroethyl, trichloroethyl, dichlorodifluoroethyl, pentafluoroethyl, heptafluoropropyl, nonafluorobutyl, decafluoropentyl, tridecafluorohexyl, pentadecafluoroheptyl, heptadecafluorooctyl, cyanomethyl, hydroxylmethyl, 1-hydroxyethyl, 2-hydroxyethyl, 3-hydroxypropyl, 3-hydroxybutyl, 4-hydroxybutyl, and 1,2-dihydroxyethyl.

Examples of the optionally substituted C6-C20 aryl group represented by $R^{41}$ through $R^{50}$ and $R^{58}$ in formula (III) include phenyl, naphthyl, 2-methylphenyl, 3-methylphenyl, 4-methylphenyl, 4-vinylphenyl, 3-isopropylphenyl, 4-isopropylphenyl, 4-butylphenyl, 4-isobutylphenyl, 4-t-butylphenyl, 4-hexylphenyl, 4-cyclohexylphenyl, 4-octylphenyl, 4-(2-ethylhexyl)phenyl, 4-stearylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4-di-t-butylphenyl, cyclohexylphenyl, and hydroxyphenyl.

Examples of the optionally substituted C7-C20 arylalkyl group represented by $R^{41}$ through $R^{50}$ and $R^{58}$ in formula (III) include benzyl, phenethyl, phenacyl, 2-phenylpropan-2-yl, diphenylmethyl, triphenylmethyl, styryl, cinnamyl, 2-hydroxybenzyl, 3-hydroxybenzyl, 4-hydroxybenzyl, 2-hydroxyphenethyl, 3-hydroxyphenethyl, 4-hydroxyphenethyl, 2-hydroxyphenacyl, 3-hydroxyphenacyl, 4-hydroxyphenacyl, 2-phenoxyethyl, and 2-phenylthioethyl.

The methylene chain in the alkyl, aryl, and arylalkyl groups may be interrupted by —O—, —S—, —CO—, —CO—O—, or —O—CO—. Examples of such interrupted groups include optionally substituted C1-C18 alkoxy, optionally substituted C6-C20 aryloxy, optionally substituted C1-C18 thioalkoxy, optionally substituted C6-C20 thiophenoxy, and optionally substituted C1-C12 ester groups.

Examples of the optionally substituted C1-C18 alkoxy include methoxy, ethoxy, propoxy, isopropoxy, butoxy, s-butoxy, t-butoxy, isobutoxy, pentyloxy, isoamyloxy, t-amyloxy, hexyloxy, cyclohexyloxy, cyclohexylmethyloxy, tetrahydrofuranyloxy, tetrahydropyranyloxy, hydroxymethyloxy, 1-hydroxyethyloxy, 2-hydroxyethyloxy, 3-hydroxypropyloxy, 2-hydroxypropyloxy, 2,3-dihydroxypropyloxy, 2-hydroxy-1-methylethyloxy, 2-hydroxybutyloxy, 4-hydroxybutyloxy, 2,3-dihydroxybutyloxy, 3,4-dihydroxybutyloxy, 2,3,4-trihydroxybutyloxy, 2-(2-hydroxyethyloxy)ethyloxy, 2-hydroxy-3-methoxypropyloxy, 5-hydroxypentyloxy, 2-hydroxy-2-(hydroxymethyl)butyloxy, 3-hydroxy-2-di(hydroxymethyl)propyloxy, 6-hydroxyhexyloxy, 5,6-dihydroxyhexyloxy, 2-hydroxycyclohexyloxy, 4-hydroxycyclohexyloxy, 2,3,4,5,6-pentahydroxycyclohexyloxy, 2-(2-(2-hydroxyethyloxy)ethyloxy)ethyloxy, 4-hydroxymethylcyclohexylmethyloxy, and 2-di(hydroxymethyl)butyloxy.

Examples of the optionally substituted C6-C20 aryloxy are phenoxy and hydroxyphenyloxy.

Examples of the optionally substituted C1-C18 thioalkoxy include methylthio, ethylthio, propylthio, isopropylthio, butylthio, s-butylthio, t-butylthio, isobutylthio, amylthio, isoamylthio, t-amylthio, hexylthio, cyclohexylthio, adamantylthio, 2-hydroxyethylthio, 3-hydroxypropylthio, 2,3-dihydroxypropylthio, and 2-hydroxy-1-methylpropylthio.

Examples of the optionally substituted C6-C20 thiophenoxy are phenylthio and hydroxyphenylthio.

Examples of the optionally substituted C1-C12 ester group include methoxycarbonyl, ethoxycarbonyl, isopropyloxycarbonyl, phenoxycarbonyl, acetoxy, methoxyacetyloxy, propionyloxy, butyryloxy, t-butylcarbonyloxy, benzoyloxy, adamantylcarbonyloxy, 2-hydroxyethoxycarbonyl, 3-hydroxypropyloxycarbonyl, 4-hydroxyphenoxycarbonyl, 3-hydroxypropionyloxy, 4-hydroxybutyryloxy, and 4-hydroxybenzoyloxy.

The C1-C18 alkyl represented by $R^{41}$ to $R^{58}$ in formula (III), the C1-C18 alkoxy represented by $R^{41}$ to $R^{58}$ in formula (III), the C1-C18 thioalkoxy represented by $R^{41}$ to $R^{58}$ in formula (III), the C1-C12 ester group represented by $R^{41}$ to $R^{58}$ in formula (III), the C6-20 aryl represented by $R^{41}$ to $R^{50}$ and $R^{58}$ in formula (III), the C7-C20 arylalkyl represented by $R^{41}$ to $R^{50}$ and $R^{58}$ in formula (III), C6-C20 aryloxy represented by $R^{41}$ to $R^{50}$ and $R^{58}$ in formula (III), and the C6-C20 thiophenoxy represented by $R^{41}$ to $R^{50}$ and $R^{58}$ in formula (III) may have a substituent.

Examples of the substituent include alkyl, such as methyl, ethyl, propyl, isopropyl, butyl, isobutyl, t-butyl, pentyl, isopentyl, t-pentyl, neopentyl, hexyl, isohexyl, heptyl, octyl, 2-ethylhexyl, nonyl, decyl, undecyl, dodecyl, tridecyl, isotridecyl, myristyl, palmityl, stearyl, cyclopropyl, cyclohexyl, 1-adamantyl, 2-adamantyl, 2-methyl-1-adamantyl, 2-methyl-2-adamantyl, 2-ethyl-1-adamantyl, 2-ethyl-2-adamantyl, 2-norbornyl, 2-norbornylmethyl, camphor-10-yl vinyl, allyl, isopropenyl, 1-propenyl, 2-methoxy-1-propenyl, fluoromethyl, difluoromethyl, trifluoromethyl, chloromethyl, dichloromethyl, trichloromethyl, bromomethyl, dibromomethyl, tribromomethyl, difluoroethyl, trichloroethyl, dichlorodifluoroethyl, pentafluoroethyl, heptafluoropropyl, nonafluorobutyl, decafluoropentyl, tridecafluorohexyl, pentadecafluoroheptyl, heptadecafluorooctyl, methoxymethyl, methoxyethoxymethyl, methylthiomethyl, ethoxyethyl, butoxymethyl, t-butylthiomethyl, 4-pentenyloxymethyl, trichloroethoxymethyl, bis(2-chloroethoxy)methyl, methoxycyclohexyl, 1-(2-chloroethoxy)ethyl, methoxyethyl, 1-methyl-1-methoxyethyl, ethyldithioethyl, trimethylsilylethyl, t-butyldimethylsilyloxymethyl, 2-(trimethylsilyl)ethoxymethyl, t-butoxycarbonylmethyl, ethyloxycarbonylmethyl, ethylcarbonylmethyl, t-butoxycarbonylmethyl, acryloyloxyethyl, methacryloyloxyethyl, 2-methyl-2-adamantyloxycarbonylmethyl, and acetylethyl; aryl, such as phenyl, 1-naphthyl, 2-naphthyl, anthracen-1-yl, phenanthren-1-yl, o-tolyl, m-tolyl, p-tolyl, 4-vinylphenyl, ethylphenyl, propylphenyl, 3-isopropylphenyl, 4-isopropylphenyl, 4-butylphenyl, 4-isobutylphenyl, 4-t-butylphenyl, 4-hexylphenyl, 4-cyclohexylphenyl, 4-octylphenyl, 4-(2-ethylhexyl)phenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4-di-t-butylphenyl, 2,5-di-t-butylphenyl, 2,6-di-t-butylphenyl, 2,4-di-t-pentylphenyl, 2,5-di-t-amylphenyl, cyclohexylphenyl, biphenylyl, 2,4,5-trimethylphenyl, 9-fluorenyl, 4-chlorophenyl, 3,4-dichlorophenyl, 4-trichlorophenyl, 4-trifluorophenyl, fluorophenyl, trifluoromethylphenyl, pentafluorophenyl, heptafluoro-p-tolyl, 4-formylphenyl, 4-nitrophenyl, ethoxynaphthyl, 4-fluoromethylphenyl, 4-methoxyphenyl, and 2,4-dinitrophenyl; arylalkyl, such as benzyl, methylbenzyl, dimethylbenzyl, trimethylbenzyl, phenylbenzyl, diphenylmethyl, triphenylmethyl, 2-phenylethyl, 2-phenylpropyl, styryl, cinnamyl, fluorobenzyl, chlorobenzoyl, bromobenzyl, cyanobenzyl, dichlorobenzyl, methoxybenzyl, dimethoxybenzyl, benzyloxymethyl, methoxybenzyloxymethyl, 1-methyl-1-benzyloxyethyl, 1-methyl-1-benzyloxy-2-fluoroethyl, guaiacolmethyl, phenoxymethyl, phenylthiomethyl, nitrobenzyl, dinitrobenzhydryl, dibenzosuberyl, (phenyldimethylsilyl)methoxymethyl, phenylsulfonylethyl, triphenylphosphonioethyl, triphenylmethoxymethyl, phenacyl, and bromophenacyl; alkoxy represented by RO—, acyl represented by RCO—, ester group represented by RCOO— or ROCO—, carbonate represented by ROCOO—, sulfanyl represented by RS—, sulfinyl represented by RSO—, sulfonyl represented by RSO$_2$—, and sulfonic ester group represented by RSO$_3$—, wherein R represents the alkyl, aryl, or arylalkyl group described or a heterocyclic group, such as tetrahydropyranyl, 3-bromotetrahydropyranyl, tetrahydrothiopyranyl, methoxytetrahydropyranyl, methoxytetrahydrothiopyranyl, 4-methoxytetrahydrothiopyran-S,S-dioxide-4-yl, 1-[(2-chloro-4-methyl)phenyl]-4-methoxypiperidin-4-yl, 1,4-dioxan-2-yl, tetrahydrofuranyl, tetrahydrothiofuranyl, 2,3,3a,4,5,6,7,7a-octahydro-7,8,8-trimethyl-4,7-metanobenzofuran-2-yl, 2-pyridylmethyl, 4-pyridylmethyl, 3-picolin-N-oxide-2-ylmethyl, 1,3-benzodithioranyl, benzisothiazolin-S,S-dioxide-3-yl, and tetrafluoro-4-pyridyl; formyl; carboxyl; formyloxy; sulfo; silyloxy, such as trimethylsilyloxy, triethylsilyloxy, tripropylsilyloxy, dimethylpropylsilyloxy, diethylpropylsilyloxy, dimethyl(1,1,2,2-tetramethyl)ethylsilyloxy, butyldimethylsilyloxy, butyldiphenylsilyloxy, tribenzylsilyloxy, trixylylsilyloxy, triphenylsilyloxy, diphenylmethylsilyloxy, and butylmethoxyphenylsilyloxy; phosphoric ester group; benzylthiocarbonate; methyldithiocarbonate; hydroxyl; nitro; and halogen, such as fluorine, chlorine, bromine, or iodine.

Examples of the anion represented by X$_3^-$ in formula (III) include halide anions, such as chloride, bromide, iodide, and fluoride; inorganic anions, such as perchlorate, chlorate, thiocyanate, hexafluorophosphate, hexafluoroantimonate, hexafluoroarsenate, and tetrafluoroborate; organic sulfonate anions, such as methanesulfonate, fluorosulfonate, benzenesulfonate, toluenesulfonate, 1-naphthylsulfonate, 2-naphthylsulfonate, trifluoromethanesulfonate, pentafluoroethanesulfonate, heptafluoropropanesulfonate, nonafluorobutanesulfonate, undecafluoropentanesulfonate, tridecafluorohexanesulfonate, pentadecafluoroheptanesulfonate, heptadecafluorooctanesulfonate, perfluoro-4-ethylcyclohexanesulfonate, N-alkyl(or aryl)diphenylamine-4-sulfonate, 2-amino-4-methyl-5-chlorobenzenesulfonate, 2-amino-5-nitrobenenesulfonate, the sulfonate described in JP 2004-53799A, camphorsulfonate, fluorobenzenesulfonate, difluorobenzenesulfonate, trifluorobenzenesulfonate, tetrafluorobenzenesulfonate, and pentafluorobenzenesulfonate; organic phosphonate anions, such as octylphosphonate, dodecylphosphonate, octadecylphosphonate, phenylphosphonate, nonylphenylphosphonate, and 2,2'-methylenebis(4,6-di-t-butylphenyl)phosphonate; organic fluorosulfonimide ions, such as bis(trifluoromethanesulfone)imide ion, bis(pentafluoroethanesulfone)imide ion, bis(heptafluoropropanesulfone)imide ion, bis(nonafluorobutanesulfone)imide ion, bis(undecafluoropentanesulfone)imide ion, bis(pentadecafluoroheptanesulfone)imide ion, bis(tridecafluorohexanesulfone)imide ion bis(heptadecafluorooctanesulfonimide) ion, (trifluoromethanesulfone)(nonafluorobutanesulfone)imide ion, (methanesulfone) (trifluoromethanesulfone)imide ion, and cyclohexafluoropropane-1,3-bis(sulfonyl)imide ion; tetraarylborate anions, such as tetrakis(pentafluorophenyl)borate ion, tetrakis(4-fluorophenyl)borate ion, tetraphenylborate ion, the borate ions described in JP 2007-112854A, JP 6-184170A, JP 2002-526391A, and JP 2007-285538A; various aliphatic or aromatic carboxylate anions; and organic sulfonylmethide ions, such as tris(trifluoromethanesulfonyl)methide and tris(methanesulfonyl)methide. Also included are alkylsulfonate ions, fluoro-substituted alkylsulfonate ions, and alkylsulfonimides or fluoro-substituted alkylsulfonimides substituted with acryloyloxy, methacryloyloxy, or aliphatic cycloalkyl, such as norbornyl or adamantyl. If desired, a quencher anion capable of deexciting (quenching) an active molecule in an excited state or a metallocene compound anion of, for example, a ferrocene or ruthenocene compound having an anionic group (e.g., a carboxyl group, a phosphonic acid group, or a sulfonic acid group) on its cyclopentadienyl ring may be used. Of these anions preferred are organic sulfonate anions in view of safety and reactivity (in both deprotection reaction and crosslinking reaction).

Specific examples of the cation of the aromatic sulfonium salt compound represented by formula (III) include the following cations numbered from 17 through 26:

[Chem. 6]

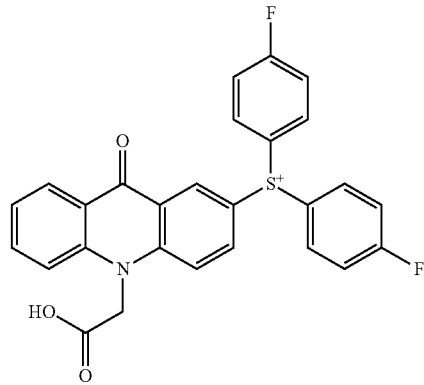

No. 17

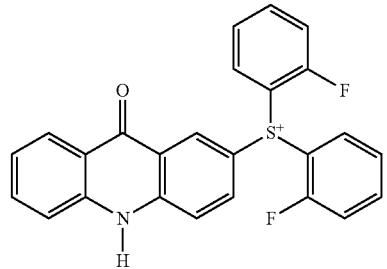

No. 18

-continued
No. 19
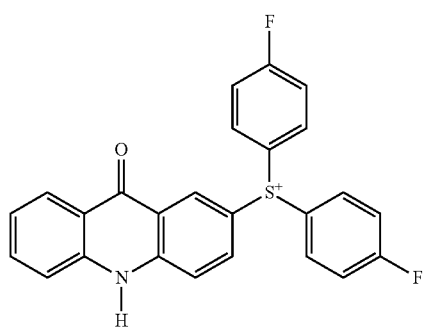
No. 20
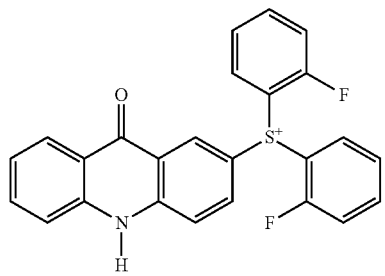
No. 21
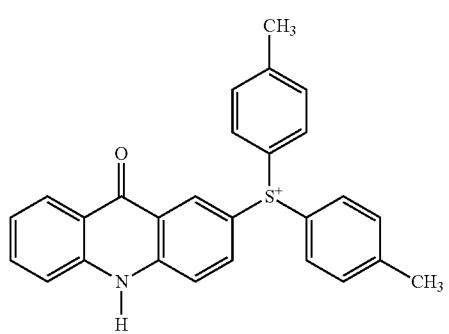
No. 22
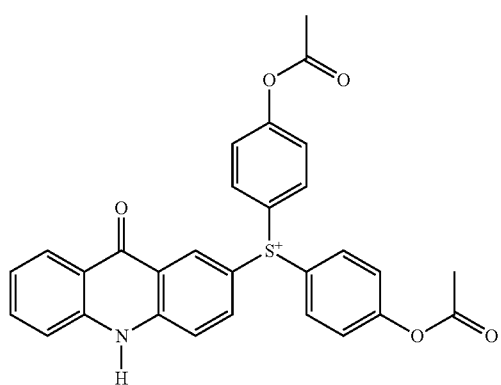
-continued
No. 23
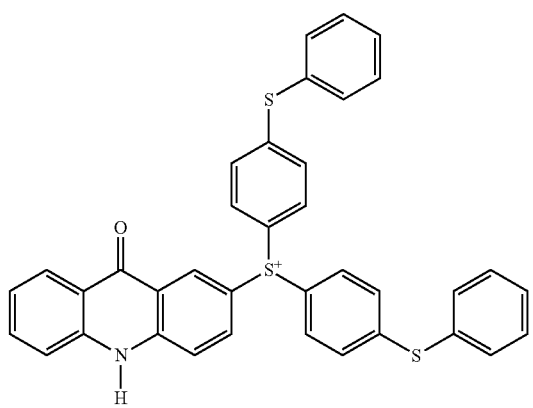
No. 24
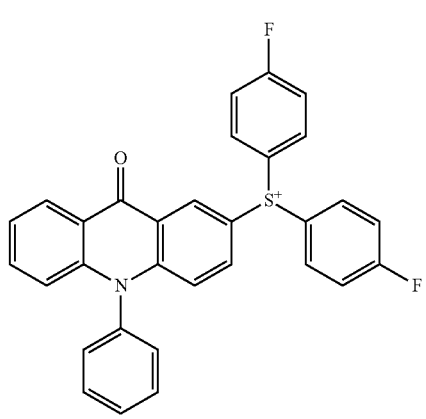
No. 25
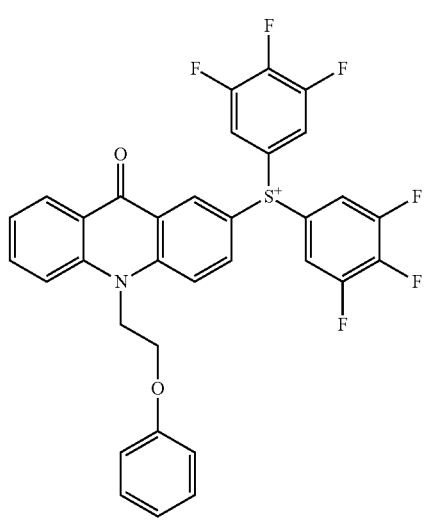

-continued

No. 26

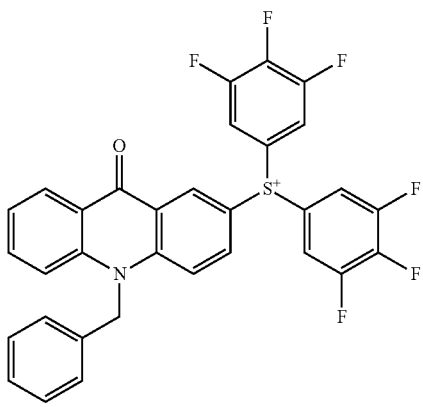

Of the compounds represented by formula (I) or (III), those represented by general formula (IV) below are preferred to provide a photo-acid generator having high acid generating ability.

[Chem. 7]

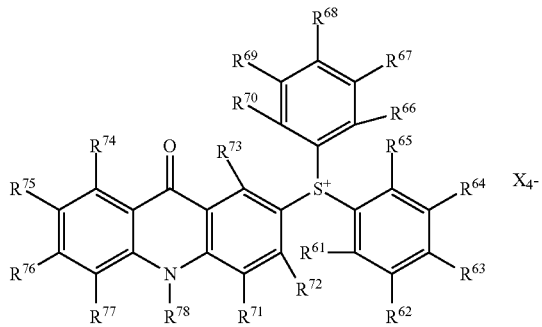

(IV)

wherein $R^{61}$, $R^{62}$, $R^{63}$, $R^{64}$, $R^{65}$, $R^{66}$, $R^{67}$, $R^{68}$, $R^{69}$ and $R^{70}$ each independently represent a hydrogen atom, a halogen atom, a hydroxyl group, a nitro group, an optionally substituted alkyl group having 1 to 18 carbon atoms, an optionally substituted aryl group having 6 to 20 carbon atoms, or an optionally substituted arylalkyl group having 7 to 20 carbon atoms;

$R^{71}$, $R^{72}$, $R^{73}$, $R^{74}$, $R^{75}$, $R^{76}$, and $R^{77}$ each independently represent a hydrogen atom, a halogen atom, a hydroxyl group, a nitro group, or an optionally substituted alkyl group having 1 to 18 carbon atoms;

$R^{78}$ represents an optionally substituted aryl group having 6 to 20 carbon atoms or an optionally substituted arylalkyl group having 7 to 20 carbon atoms;

the number of optional substituents when present on the C1-C18 alkyl group represented by $R^{61}$ through $R^{77}$, the C6-C20 aryl group represented by $R^{61}$ through $R^{70}$ and $R^{78}$, and the C7-C20 arylalkyl group represented by $R^{61}$ through $R^{70}$ and $R^{78}$ being not limited;

the methylene chain of the C1-C18 alkyl group represented by $R^{61}$ through $R^{77}$, the C6-C20 aryl group represented by $R^{61}$ through $R^{70}$ and $R^{78}$, and the C7-C20 arylalkyl group represented by $R^{61}$ through $R^{70}$ and $R^{78}$ being optionally interrupted by —O—, —S—, —CO—, —CO—O—, or —O—CO—; and $X_4^-$ represents a monovalent anion.

Examples of the halogen atom represented by $R^{61}$ to $R^{77}$ in formula (IV), the optionally substituted C1-C18 alkyl represented by $R^{61}$ to $R^{77}$ in formula (IV), the optionally substituted C6-C20 aryl represented by $R^{61}$ to $R^{70}$ and $R^{78}$ in formula (IV), the optionally substituted C7-C20 arylalkyl represented by $R^{61}$ to $R^{70}$ and $R^{78}$ in formula (IV), and the anion represented by $X_4^-$ in formula (IV) are the same as those enumerated with respect to the formula (III).

Of the compounds represented by formulae (I) or (III), those of formula (V) are preferred to provide a photo-acid generator having high solubility in a solvent and achieving high developing properties.

[Chem. 8]

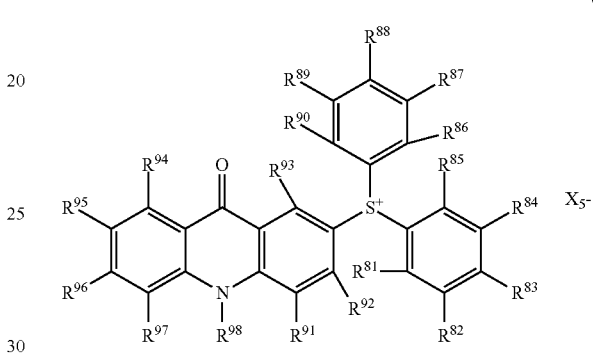

(V)

wherein $R^{81}$, $R^{82}$, $R^{83}$, $R^{84}$, $R^{85}$, $R^{86}$, $R^{87}$, $R^{88}$, $R^{89}$, and $R^{90}$ each independently represent a hydrogen atom, a halogen atom, a hydroxyl group, a nitro group, an optionally substituted alkyl group having 1 to 18 carbon atoms, an optionally substituted aryl group having 6 to 20 carbon atoms, or an optionally substituted arylalkyl group having 7 to 20 carbon atoms;

$R^{91}$, $R^{92}$, $R^{93}$, $R^{94}$, $R^{95}$, $R^{96}$, and $R^{97}$ each independently represent a hydrogen atom, a halogen atom, a hydroxyl group, a nitro group, or an optionally substituted alkyl group having 1 to 18 carbon atoms;

$R^{98}$ represents a hydrogen atom, a substituted alkyl group having 1 to 10 carbon atoms, an optionally substituted alkyl group having 11 to 18 carbon atoms, an optionally substituted aryl group having 6 to 20 carbon atoms, or an optionally substituted arylalkyl group having 7 to 20 carbon atoms;

the number of optional substituents when present on the C1-C18 alkyl group represented by $R^{81}$ through $R^{98}$, the C6-C20 aryl group represented by $R^{81}$ through $R^{90}$ and $R^{98}$, and the C7-C20 arylalkyl group represented by $R^{81}$ through $R^{90}$ and $R^{98}$ being not limited;

the methylene chain of the C1-C18 alkyl group represented by $R^{81}$ through $R^{98}$, the C6-C20 aryl group represented by $R^{81}$ through $R^{90}$ and $R^{98}$, and the C7-C20 arylalkyl group represented by $R^{81}$ through $R^{90}$ and $R^{98}$ being optionally interrupted by —O—, —S—, —CO—, —CO—O—, or —O—CO—; and $X_5^-$ represents a monovalent anion;

provided that at least one of $R^{81}$ through $R^{98}$ is a hydroxyl group, a hydroxyl-substituted alkyl group having 1 to 18 carbon atoms, a hydroxyl-substituted aryl group, or a hydroxyl-substituted arylalkyl group.

Examples of the halogen atom represented by $R^{81}$ to $R^{97}$ in formula (V), the optionally substituted C1-C18 alkyl represented by $R^{81}$ to $R^{97}$ in formula (V), the optionally substituted C6-C20 aryl represented by $R^{81}$ to $R^{90}$ and $R^{98}$ in formula (V), the optionally substituted C7-C20 arylalkyl represented by $R^{81}$ to $R^{90}$ and $R^{98}$ in formula (V), and the anion represented by $X_5^-$ in formula (V) are the same as those enumerated with respect to the formula (III).

Specific examples of the cation of the aromatic sulfonium salt compound represented by formula (IV) or (V) include the following cations numbered from 27 to 36:

[Chem. 9]

No. 27
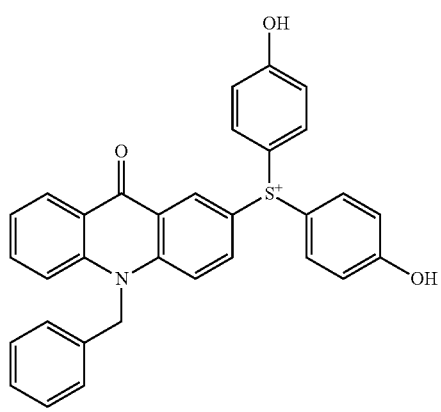

No. 28
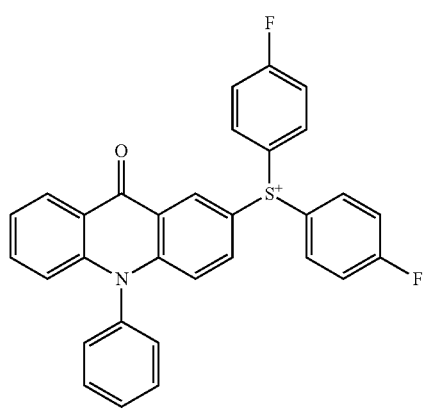

No. 29
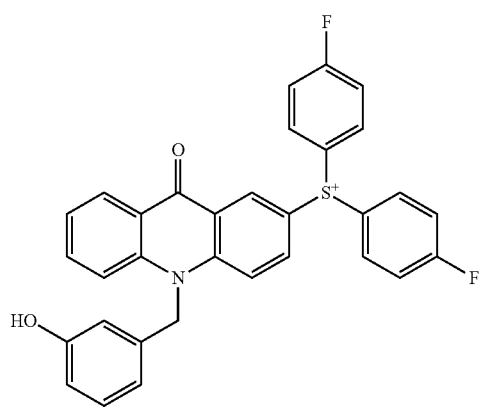

No. 30
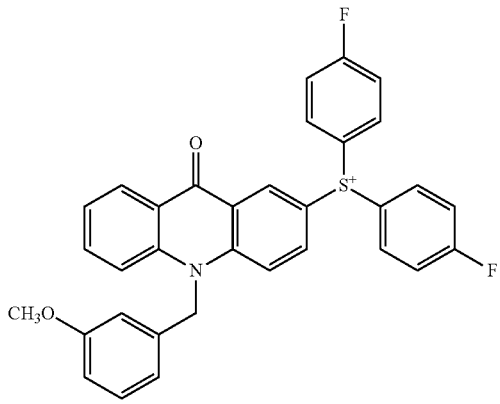

No. 31
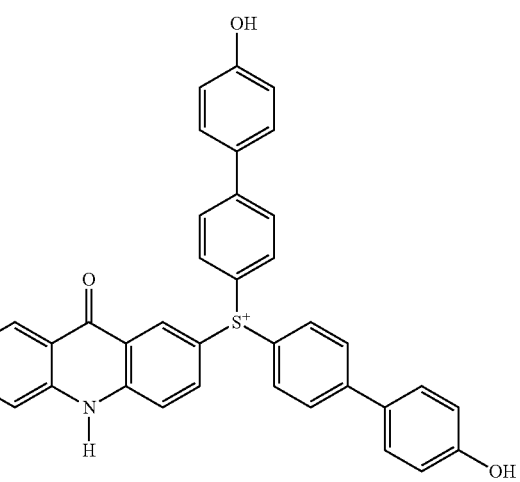

No. 32
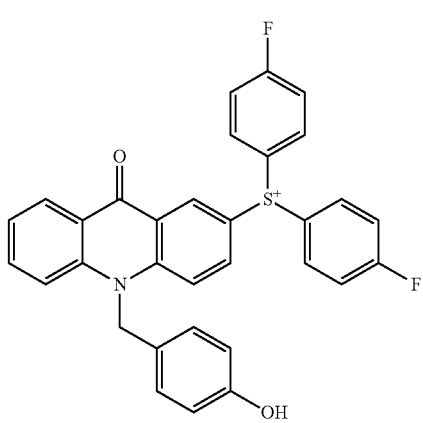

No. 33

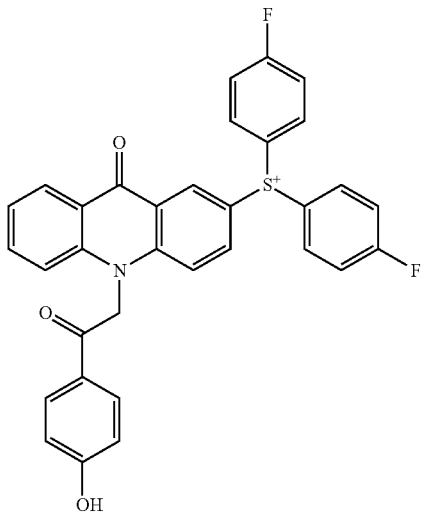

No. 34

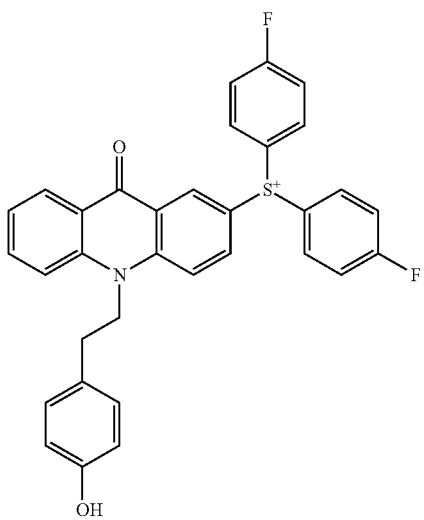

No. 35

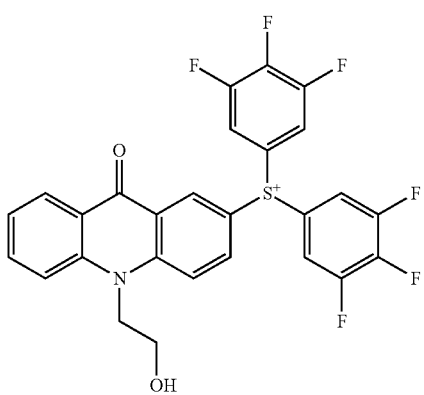

No. 36

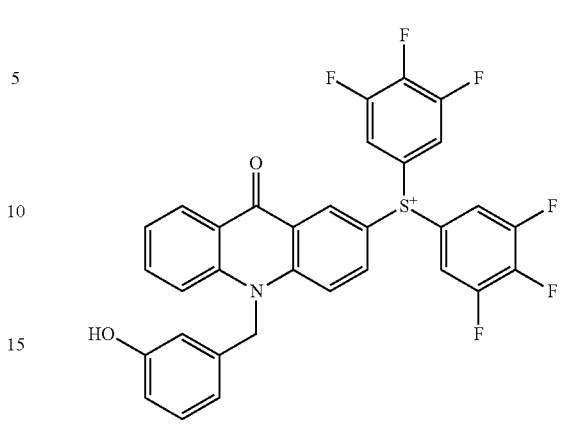

Of the aromatic sulfonium salt compounds of formula (II) preferred are those in which at least one of $R^{21}$, $R^{22}$, $R^{23}$, $R^{24}$, $R^{25}$, $R^{26}$, $R^{27}$, $R^{28}$, $R^{29}$, and $R^{30}$ is a hydroxyl group for their high developing properties and acid generating ability.

Of the aromatic sulfonium salt compounds of formula (III) preferred are those in which at least one of $R^{41}$, $R^{42}$, $R^{43}$, $R^{44}$, $R^{45}$, $R^{46}$, $R^{47}$, $R^{48}$, $R^{49}$, and $R^{50}$ is a halogen atom or a hydroxyl group, and $R^{58}$ is a hydroxyl-substituted C6-C20 aryl or hydroxyl-substituted C7-C20 arylalkyl group for their high developing properties and acid generating ability.

The aromatic sulfonium salt compound of the invention may be prepared by any process utilizing known organic synthesis reactions. For example, the aromatic sulfonium salt compound of the invention is obtained by the reaction between a diaryl sulfoxide compound and an acridone compound to obtain a sulfonium salt compound, which is, if necessary, subjected to salt exchange with a salt compound having a desired anion component.

The aromatic sulfonium salt compound of the invention has the property of generating a Lewis acid on exposure to active energy radiation, such as extreme ultraviolet light (EUV), X-rays, deep ultraviolet light (DUV) (e.g., $F_2$, ArF, or KrF laser light, i-line, h-line, or g-line), electron beam, radiation, and high frequency waves, and is capable of acting on an acid-reactive organic substance to induce decomposition or polymerization. Therefore, the sulfonium salt compound of the invention is useful as a photo-acid generator of a positive or negative photoresist or a cationic polymerization initiator.

The photo acid generator of the invention comprises the above described aromatic sulfonium salt compound. The photo acid generator of the invention is used in the polymerization of a cationically polymerizable compound, which an acid reactive organic substance, cleavage of the chemical bond (e.g., ester or ether linkage) of acrylic resins, and the like. The amount of the photo acid generator to be used for an acid reactive organic substance is preferably, but not limited to, 0.05 to 100 parts, more preferably 0.05 to 20 parts, by mass per 100 parts by mass of the acid reactive organic substance. The amount may be out of the range recited depending on the properties of the acid reactive organic substance and other factors, such as the irradiation intensity, reaction time, desired physical properties, and cost.

Useful acid reactive organic substances include hereinafter-described resins that change their solubility in a developer by the action of an acid (hereinafter referred to as resist base resins) and stereolithographic resins.

The resist composition according to the invention contains a resist base resin as an acid reactive organic substance and the aromatic sulfonium salt compound of the invention as an essential photo acid generator.

The resist base resin for use in the resist composition of the invention is not particularly limited but is preferably a resin having a small extinction coefficient for the wavelength of active energy radiation used and exhibiting high etching resistance.

Examples of such resist base resins include one or more polymers selected from polyhydroxystyrene and its derivatives; polyacrylic acid and its derivatives; polymethacrylic acid and its derivatives; copolymers obtained from at least two of hydroxystyrene, acrylic acid, methacrylic acid, and their derivatives; copolymers obtained from at least two of hydroxystyrene, styrene, and their derivatives; copolymers obtained from at least three of a cycloolefin and its derivatives, maleic anhydride, and acrylic acid and its derivatives; copolymers obtained from at least three of a cycloolefin and its derivatives, maleimide, and acrylic acid and its derivatives; polynorbornene; and ring-opening metathesis polymers; as well as the polymers enumerated above partially substituted by an acid-labile group showing alkali-solubility controlling ability. Examples of the acid-labile group to be introduced into the polymer include tertiary alkyl, trialkylsilyl, oxoalkyl, aryl-substituted alkyl, alicyclic heterocyclic (e.g., tetrahydropyran-2-yl), tertiary alkylcarbonyl, tertiary alkylcarbonylalkyl, and alkyloxycarbonyl groups.

Detailed description and specific examples of the resist base resin are described, e.g., in claims 8 to 11 of JP 2003-192665A, claim 3 of JP 2004-323704A, and JP 10-10733A.

The polystyrene equivalent weight average molecular weight (Mw) of the resist base resin measured by gel permeation chromatography is usually 1,500 to 300,000, preferably 2,000 to 200,000, even more preferably 3,000 to 100,000. Using a base resin having an Mw of less than 1,500 tends to provide a resist with reduced heat resistance. Using a base resin having an Mw of more than 300,000 tends to provide a resist with reduced developability and coating properties.

The photo acid generator in the resist composition of the invention may contain other photo acid generator in addition to the aromatic sulfonium salt compound of the invention. To secure sensitivity and developability as a resist, the amount of the photo acid generator in the resist composition is usually 0.01 to 20 parts, preferably 0.5 to 10 parts, by mass per 100 parts by mass of the resist base resin. When the amount of the photo acid generator is less than 0.01 parts by mass, the sensitivity and developability of the resulting resist can be reduced. When it is more than 20 parts, the resist can have reduced transparency to radiation, resulting in difficulty in providing a resist pattern having a rectangular cross-section.

Examples of the other photo acid generator that may be used in combination with the aromatic sulfonium salt compound of the invention include iodonium salt compounds and sulfonylimide compounds. The amount of the photo acid generator other than the aromatic sulfonium salt compound, when used in combination, is preferably not more than 50 parts by mass per 100 parts by mass of the aromatic sulfonium salt compound of the invention.

The photo acid generator comprising the aromatic sulfonium salt compound may be compounded into the resist composition of the invention along with various additives as well as the other photo acid generator. Such additives include inorganic fillers, organic fillers, colorants including pigments and dyes, defoaming agents, thickening agents, flame retardants, antioxidants, stabilizers, and leveling agents. The total content of these additives in the resist composition is preferably 50% by mass or less.

On use, the resist composition of the invention is usually adjusted in concentration by diluting with a solvent to a total solids concentration usually of from 5 to 50%, preferably of from 10 to 25%, by weight, followed by filtration through a filter having an opening size of about 0.2 μm. The resist composition of the invention is prepared by mixing the photo acid generator comprising the aromatic sulfonium salt compound, the other photo acid generator, the resist base resins, and the other optional components by dissolving, kneading, or otherwise.

The resist composition of the invention is particularly useful as a chemically amplified resist. Chemically amplified resists are divided into negative resists in which a chemical chain reaction takes place by the action of the acid generated from the photo acid generator on exposure to light to cause the base resin to crosslink or change in polarity to be insolubilized in a developer and positive resists in which the side chain of the base resin is deprotected by the action of the acid to cause the base resin to change in polarity to be solubilized in a developer.

The light that can be used in exposure of the resist composition is selected as appropriate to the photo acid generator used from among visible light, UV light, DUV, X-rays, charged particle radiation, and so on. The invention is advantageously applied to resist compositions that can be patterned by a variety of radiation, such as DUV from a KrF excimer layer (248 nm) or an ArF excimer laser (193 nm), X-rays from synchrotron radiation, and charged particle beams, such as electron beams and EUV.

The cationically polymerizable composition of the invention comprises the aromatic sulfonium salt compound of the invention. The cationically polymerizable composition of the invention contains the cationic polymerization initiator of the invention and a cationically polymerizable compound and is useful in a broad range of application, including photoresists in making lithographic plates, letterpress plates, printed circuit boards, ICs, or LSIs; image formation, such as relief image formation and image replication; and photocuring inks, coatings, or adhesives.

The cationically polymerizable compound for use in the cationically polymerizable composition of the invention is a compound that undergoes polymerization or crosslinking reaction by the action of a cationic polymerization initiator activated on exposure to light. One or more than one cationically polymerizable compounds may be used.

The cationically polymerizable compounds typically include epoxy compounds, oxetane compounds, cyclic lactone compounds, cyclic acetal compounds, cyclic thioether compounds, spiro orthoester compounds, and vinyl compounds. One or more than one cationically polymerizable compounds may be used. Inter alia, epoxy compounds and oxetane compounds are suitable in terms of availability and handling convenience.

Suitable examples of the epoxy compounds are alicyclic epoxy compounds, aromatic epoxy compounds, and aliphatic epoxy compounds.

Examples of the alicyclic epoxy compounds include polyglycidyl ethers of polyhydric alcohols having at least one alicyclic ring and cyclohexene oxide- or cyclopentane oxide-containing compounds obtained by epoxidizing cyclohexene ring- or cyclopentane ring-containing compounds with an oxidizing agent. Specific examples thereof are hydrogenated bisphenol A diglycidyl ether, 3,4-epoxycyclohexylmethyl 3,4-epoxycyclohexanecarboxylate, 3,4-epoxy-1-methylcyclohexyl 3,4-epoxy-1-methylcyclohexanecarboxylate, 6-methyl-3,4-epoxycyclohexylmethyl 6-methyl-3,4-epoxycyclohexanecarboxylate, 3,4-epoxy-3-methylcyclohexylmethyl 3,4-epoxy-3-methylcyclohexanecarboxylate, 3,4-epoxy-5-methylcyclohexylmethyl 3,4-epoxy-5-methylcyclohexanecarboxylate, 2-(3,4-epoxycyclohexyl-5,5-spiro-3,4-epoxy)cyclohexane-metadioxane, bis(3,4-epoxycyclohexylmethyl) adipate, 3,4-epoxy-6-methylcyclohexyl carboxylate, methylenebis(3,4-epoxycyclohexane), dicyclopentadiene diepoxide, ethylenebis(3,4-epoxycyclohexane carboxylate), dioctyl epoxyhexahydrophthalate, and di(2-ethylhexyl)epoxyhexahydrophthalate.

Commercially available products that are suitably used as the alicyclic epoxy compound include UVR-6100, UVR-6105, UVR-6110, UVR-6128, and UVR-6200 from Union Carbide; Celloxide 2021, Celloxide 2021P, Celloxide 2081, Celloxide 2083, Celloxide 2085, Celloxide 2000, Celloxide 3000, Cyclomer A200, Cyclomer M100, Cyclomer M101, Epolead GT-301, Epolead GT-302, Epolead 401, Epolead 403, ETHB, and Epolead HD300 all from Daicel Chemical Industries, Ltd.; and KRM-2110 and KRM-2199 from ADEKA Corp.

Preferred of the alicyclic epoxy compounds described above are epoxy resins having a cyclohexene oxide structure in terms of curing properties (cure rate).

Examples of the aromatic epoxy compounds include polyglycidyl ethers of polyhydric phenols having at least one aromatic ring or alkylene oxide adducts thereof, such as glycidyl ethers of bisphenol A, bisphenol F, or an alkylene oxide adduct thereof, and epoxy novolak resins.

Examples of the aliphatic epoxy compounds include polyglycidyl ethers of aliphatic polyhydric alcohols or alkylene oxide adducts thereof, polyglycidyl esters of aliphatic long-chain polybasic acids, homopolymers obtained by vinyl polymerization of glycidyl acrylate or glycidyl methacrylate, and copolymers obtained by vinyl polymerization of glycidyl acrylate or glycidyl methacrylate and other vinyl monomer(s). Typical examples are polyhydric alcohol glycidyl ethers, such as 1,4-butanediol diglycidyl ether, 1,6-hexanediol diglycidyl ether, glycerol triglycidyl ether, trimethylolpropane triglycidyl ether, sorbitol tetraglycidyl ether, dipentaerythritol hexaglycidyl ether, polyethylene glycol diglycidyl ether, and polypropylene glycol diglycidyl ether; polyglycidyl ethers of polyether polyols obtained by adding one or more kinds of alkylene oxides to aliphatic polyhydric alcohols, such as propylene glycol, trimethylolpropane, and glycerol; and diglycidyl esters of aliphatic long-chain dibasic acids. Further included are monoglycidyl ethers of aliphatic higher alcohols, monoglycidyl ethers of phenol, cresol, butylphenol, or polyether alcohols obtained by adding an alkylene oxide thereto, glycidyl esters of higher fatty acids, epoxidized soybean oil, octyl epoxystearate, butyl epoxystearate, and epoxidized polybutadiene.

Commercially available products suitably used as the aromatic or aliphatic epoxy compound include Epikote 801 and Epikote 828 from Yuka Shell Epoxy Co., Ltd.; PY-306, 0163, and DY-022 from Ciba Specialty Chemicals; KRM-2720, EP-4100, EP-4000, EP-4080, EP-4900, ED-505, and ED-506 from ADEKA; Epolite M-1230, Epolite EHDG-L, Epolite 40E, Epolite 100E, Epolite 200E, Epolite 400E, Epolite 70P, Epolite 200P, Epolite 400P, Epolite 1500NP, Epolite 1600, Epolite 80MF, Epolite 100MF, Epolite 4000, Epolite 3002, and Epolite FR-1500 from Kyoeisha Chemical; and Santoto ST0000, YD-716, YH-300, PG-202, PG-207, YD-172, and YDPN638 from Tohto Kasei Co., Ltd.

Examples of the oxetane compounds include 3-ethyl-3-hydroxymethyloxetane, 3-(meta)allyloxymethyl-3-ethyloxetane, (3-ethyl-3-oxetanylmethoxy)methylbenzene, 4-fluoro-[1-(3-ethyl-3-oxetanylmethoxy)methyl]benzene, 4-methoxy-[1-(3-ethyl-3-oxetanylmethoxy)methyl]benzene, [1-(3-ethyl-3-oxetanylmethoxy)ethyl]phenyl ether, isobutoxymethyl (3-ethyl-3-oxetanylmethyl)ether, isobornyloxyethyl (3-ethyl-3-oxetanylmethyl)ether, isobornyl (3-ethyl-3-oxetanylmethyl)ether, 2-ethylhexyl (3-ethyl-3-oxetanylmethyl)ether, ethyldiethylene glycol (3-ethyl-3-oxetanylmethyl)ether, dicyclopentadiene (3-ethyl-3-oxetanylmethyl)ether, dicyclopentenyloxyethyl (3-ethyl-3-oxetanylmethyl)ether, dicyclopentenyl(3-ethyl-3-oxetanylmethyl)ether, tetrahydrofurfuryl (3-ethyl-3-oxetanylmethyl)ether, tetrabromophenyl (3-ethyl-3-oxetanylmethyl)ether, 2-tetrabromophenoxyethyl (3-ethyl-3-oxetanylmethyl)ether, tribromophenyl (3-ethyl-3-oxetanylmethyl)ether, 2-tribromophenoxyethyl (3-ethyl-3-oxetanylmethyl)ether, 2-hydroxyethyl (3-ethyl-3-oxetanylmethyl)ether, 2-hydroxypropyl (3-ethyl-3-oxetanylmethyl)ether, butoxyethyl (3-ethyl-3-oxetanylmethyl)ether, pentachlorophenyl (3-ethyl-3-oxetanylmethyl)ether, pentabromophenyl (3-ethyl-3-oxetanylmethyl)ether, bornyl (3-ethyl-3-oxetanylmethyl)ether, 3,7-bis(3-oxetanyl)-5-oxa-nonane, 3,3'-(1,3,-(2-methylenyl)propanediyl-bis(oxymethylene)) bis(3-ethyloxetane), 1,4-bis[(3-ethyl-3-oxetanylmethoxy)methyl]benzene, 1,2-bis[(3-ethyl-3-oxetanylmethoxy)methyl]ethane, 1,3-bis[(3-ethyl-3-oxetanylmethoxy)methyl]propane, ethylene glycol bis(3-ethyl-3-oxetanylmethyl)ether, dicyclopentenylbis(3-ethyl-3-oxetanylmethyl)ether, triethylene glycol bis(3-ethyl-3-oxetanylmethyl)ether, tetraethylene glycol bis(3-ethyl-3-oxetanylmethyl)ether, tricyclodecanediyldimethylene (3-ethyl-3-oxetanylmethyl)ether, trimethylolpropane tris(3-ethyl-3-oxetanylmethyl)ether, 1,4-bis(3-ethyl-3-oxetanylmethoxy)butane, 1,6-bis(3-ethyl-3-oxetanylmethoxy)hexane, pentaerythritol tris(3-ethyl-3-oxetanylmethyl)ether, pentaerythritol tetrakis(3-ethyl-3-oxetanylmethyl)ether, polyethylene glycol bis(3-ethyl-3-oxetanylmethyl)ether, dipentaerythritol hexakis (3-ethyl-3-oxetanylmethyl)ether, dipentaerythritol pentakis(3-ethyl-3-oxetanylmethyl)ether, dipentaerythritol tetrakis(3-ethyl-3-oxetanylmethyl)ether, caprolactone-modified dipentaerythritol hexakis(3-ethyl-3-oxetanylmethyl)ether, caprolactone-modified dipentaerythritol pentakis(3-ethyl-3-oxetanylmethyl)ether, ditrimethylolpropane tetrakis(3-ethyl-3-oxetanylmethyl)ether, ethylene oxide-modified bisphenol A bis(3-ethyl-3-oxetanylmethyl)ether, propylene oxide-modified bisphenol A bis(3-ethyl-3-oxetanylmethyl)ether, ethylene oxide-modified hydrogenated bisphenol A bis(3-ethyl-3-oxetanylmethyl)ether, propylene oxide-modified hydrogenated bisphenol A bis(3-ethyl-3-oxetanylmethyl)ether, ethylene oxide-modified bisphenol F (3-ethyl-3-oxetanylmethyl)ether.

Use of the oxetane compound is effective and therefore preferred when, in particular, flexibility is demanded.

Examples of the other cationically polymerizable compounds include cyclic lactone compounds, such as β-propiolactone and ε-caprolactone; cyclic acetal compounds, such as trioxane, 1,3-dioxolane, and 1,3,6-trioxanecyclooctane; cyclic thioether compounds, such as tetrahydrothiophene derivatives; spiro orthoester compounds obtained by the reaction between the above described epoxy compound and a lactone; vinyl compounds, including vinyl ether compounds, such as ethylene glycol divinyl ether, alkyl vinyl ethers, 2-chloroethyl vinyl ether, 2-hydroxyethyl vinyl ether, triethylene glycol divinyl ether, 1,4-cyclohexanedimethanol divinyl ether, hydroxybutyl vinyl ether, and propylene glycol propenyl ether, and ethylenically unsaturated compounds, such as styrene, vinylcyclohexene, isobutylene, and polybutadiene; oxolane compounds, such as tetrahydrofuran and 2,3-dimethyltetrahydrofuran; thiirane compounds, such as ethylene sulfide and thioepichlorohydrin; thietane compounds, such as 1,3-propyne sulfide and 3,3-dimethylthietane; silicones; and other well-known compounds.

The amount of the cationic polymerization initiator comprising the aromatic sulfonium salt compound of the invention is preferably 0.01 to 10 parts by mass, more preferably 0.1 to 5 parts by mass, per 100 parts by mass of the cationically polymerizable compound. When the amount is less than 0.01 part by mass, undercure can result. Using more than 10 parts by mass of the initiator brings about no further increase of effects and can adversely affect the physical properties of the resulting cured product.

In addition to the cationic polymerization initiator comprising the aromatic sulfonium salt compound of the invention and the cationically polymerizable compound, the cationically polymerizable composition may further contain various additives. Useful additives include organic solvents; benzotriazole, triazine, or benzoate UV absorbers; phenol, phosphorus, or sulfur antioxidants; antistatic agents, including cationic, anionic, nonionic, or amphoteric surface active agents; flame retardants, including halogen compounds, phosphoric esters, phosphoric amides, melamine compounds, fluorine resins, metal oxides, melamine (poly)phosphates, and piperazine (poly)phosphate; lubricants including hydrocarbons, fatty acids, aliphatic alcohols, aliphatic esters, aliphatic amides, and metal soaps; colorants including dyes, pigments, and carbon black; silicic acid-based inorganic additives, such as fumed silica, fine silica powder, siliceous stone, diatomaceous earth, clay, kaolin, silica gel, calcium silicate, sericite, kaolinite, flint clay, feldspar powder, vermiculite, attapulgite, talc, mica, minnesotite, pyrophyllite, and silica; and fillers, such as glass fiber and calcium carbonate; crystallizing agents including nucleating agents and crystallization accelerators; silane coupling agents; rubber elasticity imparting agents, such as flexible polymers; and sensitizers. The total content of these additives in the cationically polymerizable composition of the invention is preferably up to 50% by mass.

To facilitate dissolving the cationic polymerization initiator in the cationically polymerizable compound, the cationic polymerization initiator may previously be dissolved in an appropriate solvent (e.g., propylene carbonate, carbitol, carbitol acetate, or butyrolactone). The cationically polymerizable composition of the invention is prepared by mixing the cationic polymerization initiator comprising the aromatic sulfonium salt compound of the invention, the cationically polymerizable compound, and other optional components by dissolving, kneading, or a like means.

The cationically polymerizable composition of the invention cures on exposure to energy radiation, such as UV light, to become dry to the touch or solvent-insoluble usually in 0.1 second to several minutes. While any energy radiation capable of inducing decomposition of the cationic polymerization initiator may be used as appropriate, it is preferred to use electromagnetic energy radiation having a wavelength of 2000 to 7000 Å emitted from an ultrahigh, high, medium, or low pressure mercury lamp, a xenon lamp, a carbon arc lamp, a metal halide lamp, a fluorescent lamp, a tungsten lamp, an excimer lamp, a germicidal lamp, an excimer laser, a nitrogen laser, an argon ion laser, a helium cadmium laser, a helium neon laser, a krypton ion laser, various semiconductor lasers, a YAG laser, a light emitting diode, an CRT, or a like light source; or high energy radiation, such as an electron beam, an X-ray, or a radiation.

An exposure time of about 0.1 to 10 seconds will generally be sufficient, while varying according to the energy radiation intensity, the coating thickness, and the cationically polymerizable organic compound. A longer exposure time would be recommended in curing a relatively thick coating. In 0.1 seconds to several minutes after the exposure, most of the compositions become dry to the touch as a result of cationic polymerization. In some cases, it is advantageous to use thermal energy by heating or from a thermal head in combination to accelerate the cationic polymerization.

EXAMPLES

Examples 1-1 to 1-7 show preparation of aromatic sulfonium salt compound Nos. 1 to 7 according to the invention. Examples 2-1 and 2-2 and Comparative Example 2-1 show evaluation on alkali developability of an alkali developable negative resist containing compound No. 1 or 5 or comparative compound No. 1. Examples 3-1 and 3-2 and Comparative Example 3-1 demonstrate evaluation of acid generation by determining the amount of acid photogenerated from compound No. 1 or 5 or comparative compound No. 1. Example 4-1 and Comparative Example 4-1 show evaluation on sensitivity to exposure of a negative resist containing compound No. 5 or comparative compound No. 1 in the form of a hexafluoroantimonate as a photo acid generator. Example 5 shows preparation of a cationically polymerizable composition containing compound No. 1 as a cationic polymerization initiator and evaluation on curing properties of the resulting composition.

Example 1-1

Synthesis of Compound No. 1

A 200 ml four-necked flask was charged with 65.44 g (0.6810 mol) of methanesulfonic acid and 6.44 g (0.0454 mol) of phosphorous pentoxide. After purging with nitrogen, the contents were heated to 100° C. to dissolve. After cooling, 9.50 g (0.0454 mol) of N-methylacridone and 10.63 g (0.0454 mol) of bis(hydroxyphenyl) sulfoxide were added thereto and caused to react at 50° C. for 4 hours. The reaction mixture was poured into a mixture of 180 g of ice water, 190 g of methanol, and 110 g of isopropyl ether in a 1 L beaker, stirred for 1 hour, and left to stand. The upper layer was discarded. To the lower layer were added 370 g of methylene chloride and 23.10 g (0.0683 mol) of potassium nonafluorobutanesulfonate, followed by stirring for 1.5 hours. The methylene chloride layer was washed with three 160 g portions of water and concentrated under reduced pressure to give 23.29 g of compound No. 1 of the invention (composed of cation No. 1 and a nonafluorobutanesulfonate anion) (yield: 70.6%; HPLC purity: 94.6%).

[Chem. 10]

Compoumd No. 1

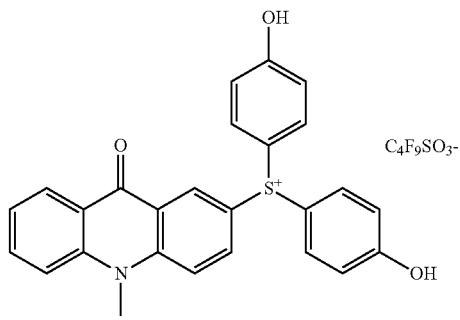

Example 1-2

Synthesis of Compound No. 2

Compound No. 2 of the invention composed of cation No. 1 and a hexafluoroantimonate anion was obtained in the same manner as in Example 1-1, except for replacing potassium nonafluorobutanesulfonate with 18.76 g (0.0683 mol) of KSbF$_6$ (yield: 5.83 g, 19.4%; HPLC purity: 96.9%).

[Chem. 11]

Compoumd No. 2

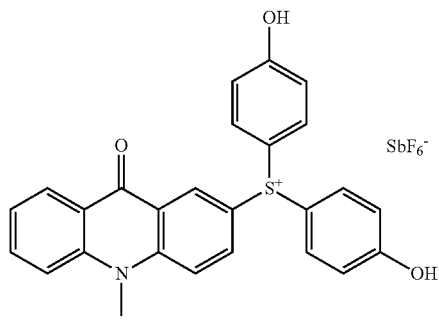

Example 1-3

Synthesis of Compound No. 3

A 200 ml four-necked flask was charged with 72.08 g (0.75 mol) of methanesulfonic acid and 7.10 g (0.05 mol) of phosphorous pentoxide. After purging with nitrogen, the contents were heated to 100° C. to dissolve. After cooling, 9.76 g (0.05 mol) of acridone was added thereto, and 11.91 g (0.05 mol) of bis(fluorophenyl) sulfoxide dissolved in 11.91 g of chlorobenzene was then added dropwise, followed by causing the system to react at 50° C. for 2 hours. The reaction mixture was poured into a mixture of 200 g of ice water, 80 g of methanol, and 200 g of toluene in a 1 L beaker, stirred for 1 hour, and left to stand. The upper layer was discarded. To the lower layer were added 200 g of methylene chloride and 9.36 g (0.06 mol) of lithium trifluoromethanesulfonate, followed by stirring for 1 hour. The methylene chloride layer was washed with three 300 ml portions of water and concentrated under reduced pressure to give 28.27 g of compound No. 3 of the invention composed of cation No. 19 and a trifluoromethanesulfonate anion (yield: 100%; HPLC purity: 95.5%).

[Chem. 12]

Compoumd No. 3

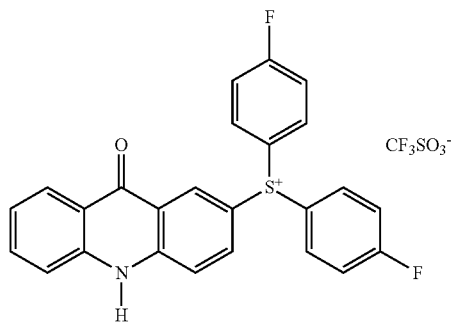

Example 1-4

Synthesis of Compound No. 4

In a 200 ml four-necked flask were put 28.27 g (0.05 mol) of compound No. 3 obtained in Example 1-3 and 64.00 g of methyl ethyl ketone and stirred to dissolve. To the solution were added 2.80 g (0.07 mol) of sodium hydroxide and 4.00 g (0.01 mol) of tetrabutylammonium hydrosulfate and stirred, followed by purging with nitrogen. While the inner temperature was kept at 30° C., 12.06 g (0.06 mol) of 3-methoxybenzyl bromide was added thereto dropwise. The inner temperature was raised to 60° C., at which the mixture was stirred for 3 hours. The reaction mixture was poured into 200 ml of methylene chloride and washed with three 100 ml portions of water. The methylene chloride layer was evaporated to remove the solvent. The resulting crude product was purified by silica gel chromatography using methylene chloride/acetone (=3/1) to give 14.29 g of compound No. 4 of the invention composed of cation No. 30 and a trifluoromethanesulfonate anion (yield: 41.7%; HPLC purity: 99.0%).

[Chem. 13]

Compoumd No.4

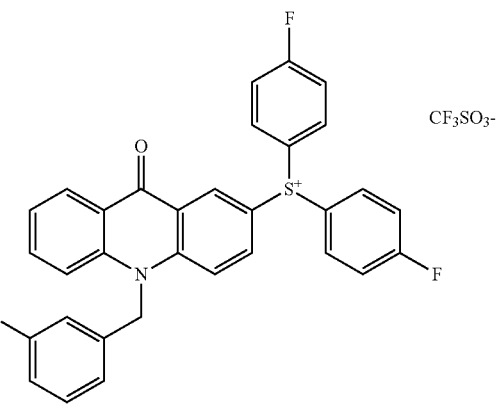

Example 1-5

Synthesis of Compound No. 5

In a 50 ml four-necked flask were put 8.00 g (0.0117 mol) of compound No. 4 obtained in Example 1-4 and 24.00 g of methylene chloride and stirred to dissolve. The solution was cooled in an isopropyl ether/dry ice bath, and 7.89 g (0.0315 mol) of boron tribromide was added thereto dropwise, followed by stiffing at room temperature for 24 hours. The reaction mixture was poured into a mixture of 200 ml of methylene chloride and 200 ml of water in a 1 L beaker, stirred for 1 hour, and allowed to stand. The aqueous layer was removed, and the methylene chloride layer was washed with three 200 ml portions of water. The solvent was removed by evaporation. The resulting crude product was purified by silica gel chromatography using methylene chloride/acetone (=3/1) to give 3.57 g of compound No. 5 of the invention composed of cation No. 29 and a trifluoromethanesulfonate anion (yield: 45.5%; HPLC purity: 98.8%).

[Chem. 14]

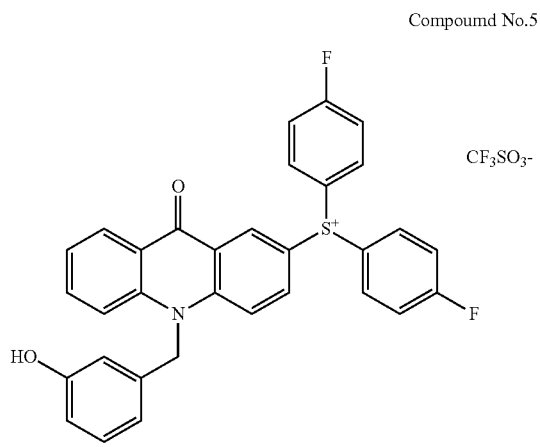

Compound No.5

Example 1-6

Synthesis of Compound No. 6

Step 1—Synthesis of Intermediate No. 6

A 50 ml four-necked flask was charged with 18.74 g (0.195 mol) of methanesulfonic acid and 1.845 g (0.013 mol) of phosphorous pentoxide. After purging with nitrogen, the contents were heated to 100° C. to dissolve. After cooling, 2.72 g (0.013 mol) of N-methylacridone and 3.10 g (0.013 mol) of bis(fluorophenyl) sulfoxide were added thereto and caused to react at 50° C. for 4 hours. The reaction mixture was poured into a mixture of 30 ml of ice water, 25 ml of methanol, and 25 ml of isopropyl ether in a 500 ml beaker, stirred for 1 hour, and allowed to stand. The upper layer was removed. To the lower layer were added 140 ml of methylene chloride and 4.64 g (0.0169 mol) of $KSbF_6$, followed by stirring for 1 hour. The methylene chloride layer was washed with three 70 g portions of water, and the solvent was removed by evaporation to afford 8.27 g of intermediate No. 6.

[Chem. 15]

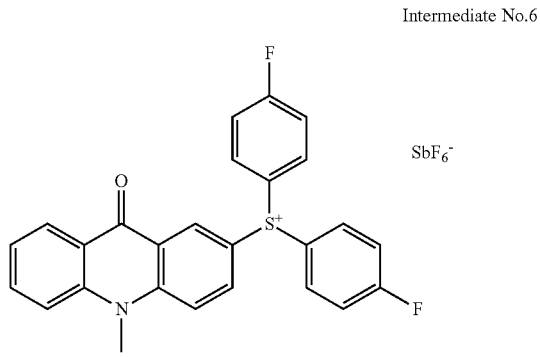

Intermediate No.6

Step 2—Synthesis of Compound No. 6

In a 30 ml four-necked flask were put 1.332 g of intermediate No. 6 obtained in step 1, 8.00 g of dimethyl sulfoxide (DMSO), 0.608 g (0.0044 mol) of potassium carbonate, and 0.034 g (0.0001 mol) of tetrabutylammonium hydrosulfate and stirred. After purging with nitrogen, 0.313 g (0.004 mol) of mercaptoethanol was added thereto dropwise, followed by stirring for 1 hour. The reaction mixture was poured into 50 ml of methylene chloride and washed with four 30 ml portions of water. The solvent was removed from the methylene chloride layer by evaporation to give 0.718 g of compound No. 6 composed of cation No. 3 and a hexafluoroantimonate anion (yield: 46.0%; HPLC purity: 93.0%).

[Chem. 16]

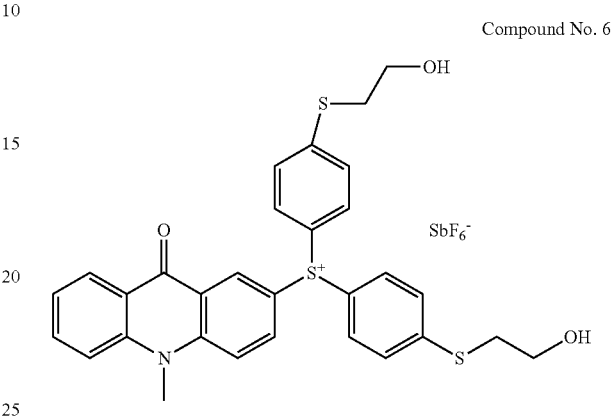

Compound No. 6

Example 1-7

Synthesis of Compound No. 7

Step 1—Synthesis of Intermediate No. 7

Intermediate No. 7 was obtained as a yellow solid in a yield of 7.03 g in the same manner as in step 1 of Example 1-6, except for replacing $KSbF_6$ with 2.64 g (0.0169 mol) of lithium trifluoromethanesulfonate.

[Chem. 17]

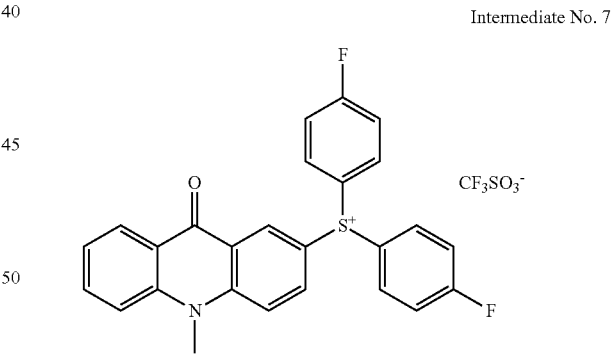

Intermediate No. 7

Step 2—Synthesis of Compound No. 7

In a 50 ml four-necked flask were put 1.159 g of intermediate No. 7 obtained in step 1 and 4.00 g of DMSO and stirred to dissolve. To the solution were added 0.216 g (0.0054 mol) of sodium hydroxide and 0.160 g (0.0004 mol) of tetrabutyl hydrosulfate. After purging with nitrogen, 1.26 g (0.01 mol) of 4hydroxythiophenol dissolved in 1.26 g of DMSO was added thereto dropwise, followed by stiffing at an inner temperature of 35° C. for 6 hours. To the reaction mixture was added 20 ml of methylene chloride, the mixture was washed with four 20 ml portions of water, and the methylene chloride layer was concentrated. To the residue was added 30 ml of methanol, followed by stirring. The thus formed precipitate was collected by filtration and dried to furnish 0.26 g of compound No. 7 composed of cation No. 8 and a trifluoromethanesulfonate anion (yield: 16%; HPLC purity: 93.8%).

[Chem. 18]

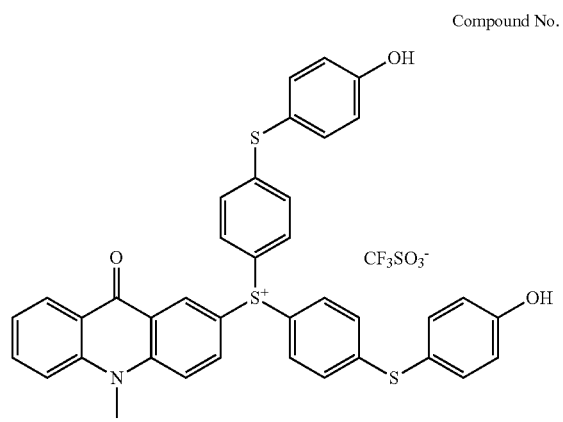

Compound No. 7

The $^1$H and $^{19}$F NMR spectral data and the results of molecular weight determination by TOF-MS of compound Nos. 1 through 7 obtained in Examples 1-1 through 1-7 are shown in Table 1 below. The position of attachment in each compound was determined by cosy, HMQC, and HMBC NMR.

TABLE 1

| Compound No. Solvent (NMR) TOF-MS, positive/negative mode | |
|---|---|
| Compound No. 1 CD$_3$OH 426.3/299.0 | 8.47(s, 1H), 8.22(d, 1H), 7.97(d, 1H), 7.88(d, 1H), 7.80(t, 1H), 7.74(d, 1H), 7.66(d, 4H), 7.33(t, 1H), 7.11(d, 4H), 3.89(s, 3H) −82.39(3F), −115.70(2F), −122.52(2F), −127.10(2F) |
| Compound No. 2 Acetone-d6 426.3/234.9, 236.9 | 9.9-10.1(s, 2H), 8.65(s, 1H), 8.43(d, 1H), 8.23(d, 1H), 8.14(d, 1H), 7.93-7.98(m, 2H), 7.83(d, 4H), 7.48(t, 1H), 7.27(d, 4H), 4.07(s, 3H) |
| Compound No. 3 Acetone-d6 416.3/149.0 | 11.67(s, 1H), 8.71(s, 1H), 8.21(d, 1H), 8.09(m, 4H), 8.03(d, 1H), 7.96(d, 1H), 7.73(t, 1H), 7.68(d, 1H), 7.63(m, 4H), 7.32(t, 1H) −78.65(3F), −103.87(2F) |
| Compound No. 4 Acetone-d6 536.4/149.0 | 8.85(s, 1H), 8.40(d, 1H), 8.18(d, 1H), 8.10(m, 4H), 7.99(d, 1H), 7.83(t, 1H), 7.73(d, 1H), 7.61(m, 4H), 7.45(t, 1H), 7.52(t, 1H), 6.87(m, 2H), 6.77(d, 1H), 5.85(s, 2H), 3.73(s, 3H) −78.70(3F), −103.99(2F) |
| Compound No. 5 DMSO-d6 522.3/149.0 | 9.39(s, 1H), 8.76(s, 1H), 8.38(d, 1H), 8.10(d, 1H), 7.97(m, 5H), 7.87(t, 1H), 7.76(d, 1H), 7.66(t, 4H), 7.46(t, 1H), 7.13(t, 1H), 6.65(m, 2H), 6.55(s, 1H), 5.79(s, 1H) −77.58(3F), −103.53(2F) |
| Compound No. 6 Acetone-d6 546.3/234.9, 236.9 | 8.75(s, 1H), 8.40(d, 1H), 8.18-8.23(m, 2H), 7.90-7.96(m, 2H), 7.83(d, 4H), 7.71(d, 4H), 7.45(t, 1H), 4.18(s, 2H), 4.10(s, 3H), 3.82(t, 4H), 3.27(t, 4H), |
| Compound No. 7 DMSO-d6 642.4/149.0 | 9.9-10.2(s, 2H), 8.59(s, 1H), 8.33(d, 1H), 8.16(d, 1H), 8.04(d, 1H), 7.90-7.96(m, 2H), 7.68(d, 4H), 7.45(t, 1H), 7.40(d, 4H), 7.28(d, 4H), 6.91(d, 4H), 3.98(s, 3H) −77.29(3F) |

Examples 2-1 and 2-2 and Comparative Example 2-1

Solubility in Polyvinylphenol/Tetramethylammonium Hydroxide (TMAH) Aqueous Solution In a screw-top tube were put 0.36 g of polyvinylphenol (S-2P from Maruzen Petrochemical Co., Ltd.; Mw: 5800) and 10.00 g of a 3% TMAH aqueous solution and heated to dissolve. A 2.00 g portion of the resulting solution was put in another screw-top tube, and a small amount of each of compound Nos. 1 and 5 and comparative compound No. 1 (intermediate No. 7 obtained in step 1 of Example 1-7) was added thereto and heated. A visual check was made to see whether the compound dissolved. This operation was repeated until saturation. The saturated solution was allowed to stand one day to make sure that no solid precipitated. The mass ratio of each compound to the polyvinylphenol of the saturated solution was taken as a parameter of solubility. The results obtained are shown in Table 2.

TABLE 2

| | Compound | Solubility (%) |
|---|---|---|
| Example 2-1 | Compound No. 1 | 70 |
| Example 2-2 | Compound No. 5 | 29 |
| Comp. Example 2-1 | Comp. Compound No. 1 | 1> |

[Chem. 19]

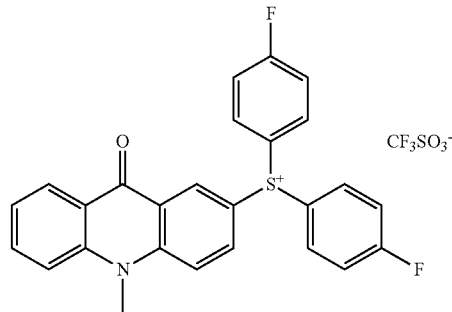

Comparative compound No. 1

It is apparent from the results in Table 2 that the aromatic sulfonium salt compound of the invention has much higher solubility than comparative compound No. 1 and superior in developing properties.

Examples 3-1 and 3-2 and Comparative Example 3-1

Evaluation on Decomposition on Exposure to Light and Resultant Acid Generation

A 0.02 mmol/g acetonitrile solution was prepared using each of compound Nos. 1 and 5 and comparative compound No. 1. A 5.00 g portion of the solution was put in a petri dish having an inner diameter of 93 mm and exposed to light of 365 nm at an irradiance of 0.8 mW/cm$^2$ for 5 minutes using a fluorescent lamp (FL10BL from Toshiba Corp.; tube length: 330 mm). The exposed solution was titrated with a 0.05 N ethanol solution of potassium hydroxide using BTB as a pH indicator. The titer as obtained was corrected by subtracting the titer of the solution before exposure determined in the same manner as a blank. The acid generation rate was calculated from the thus corrected titer according to the following formula. The results obtained are shown in Table 3.

Acid generation rate(%)=acid titer(mol)/theoretical mole number of compound(mol)×100

TABLE 3

| Compound | | Acid Generation Rate (%) |
|---|---|---|
| Example 3-1 | Compound No. 1 | 35 |
| Example 3-2 | Compound No. 2 | 19 |
| Comp. Example 3-1 | Comp. Compound No. 1 | 6.7 |

The results in Table 3 confirm that the aromatic sulfonium salt compound of the invention achieves a higher acid generation rate than the comparative compound and is therefore superior as a photo-acid generator.

Example 4-1 and Comparative Example 4-1

Preparation and Evaluation of Negative Resist Composition

Compound No. 5 and comparative compound No. 1 in the form of a hexafluoroantimonate were each synthesized. A resin solution was prepared by dissolving 100 g of EPPN-201 from Nippon Kayaku in 100 g of methyl ethyl ketone (MEK). A 0.05 g portion of each of the hexafluoroantimonate salts was dissolved in 8.00 g of the resin solution to obtain a resist solution. The resist solution was applied to an aluminum plate with a #9 bar coater and dried at 80° C. for 10 minutes. The resist was patternwise exposed to light using an ultrahigh pressure mercury lamp and a spectrometer, baked at 80° C. for 10 minutes, immersed in MEK for 30 seconds to be developed, and washed with xylene. An amount of energy of exposure required for cure was calculated from the pattern formed by irradiation with light of 405 nm. The results are shown in Table 4.

TABLE 4

| Compound | | Amount of Exposure (J/cm$^2$) |
|---|---|---|
| Example 4-1 | Compound No. 5 | 0.1 |
| Comp. Example 4-1 | Comp. Compound No. 1 | 1.9 |

The results in Table 4 confirm that a resist composition containing the aromatic sulfonium salt compound of the invention exhibits higher curability and is superior to that containing the comparative compound particularly as a negative resist composition.

Example 5

Preparation and Evaluation of Cationically Polymerizable Composition

To a mixture of 80 g of 3,4-epoxycyclohexylmethyl 3,4-epoxycyclohexylcarboxylate and 20 g of 1,4-butanediol diglycidyl ether was added 4 mmol of compound No. 1, followed by thoroughly stirring to make a uniform solution. The solution was applied to aluminum-laminated paper with a #3 bar coater and irradiated with light from an 80 W/cm$^2$ high pressure mercury lamp using an irradiator equipped with a belt conveyor. The distance between the lamp and the belt conveyor was 10 cm, and the conveying speed of the belt was 8 m/min. The cured coating was left to stand at room temperature for 24 hours and then rubbed with a cotton swab soaked in MEK. No failure of the cured coating was noted even after 200 MEK double rubs, proving sufficient progress of cure.

The invention claimed is:

1. An aromatic sulfonium salt compound represented by general formula (II):

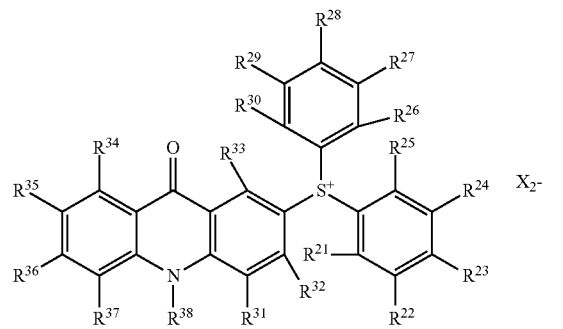

wherein $R^{21}$, $R^{22}$, $R^{22}$, $R^{24}$, $R^{28}$, $R^{26}$, $R^{27}$, $R^{28}$, $R^{28}$, and $R^{30}$ each independently represent a hydrogen atom or a hydroxyl group;
$R^{31}$, $R^{32}$, $R^{33}$, $R^{34}$, $R^{35}$, $R^{36}$, and $R^{37}$ represent a hydrogen atom;
$R^{38}$ represents a methyl group; and
$X_2^-$ represents a monovalent anion;
provided that at least one of $R^{21}$ through $R^{30}$ is a hydroxyl group.

2. A photo-acid generator composition comprising the aromatic sulfonium salt compound according to claim 1.

3. A resist composition containing the photo-acid generator according to claim 2.

4. A cationic polymerization initiator composition comprising the aromatic sulfonium salt compound according to claim 1.

5. A cationically polymerizable composition containing the cationic polymerization initiator according to claim 3.

6. An aromatic sulfonium salt compound represented by general formula (V):

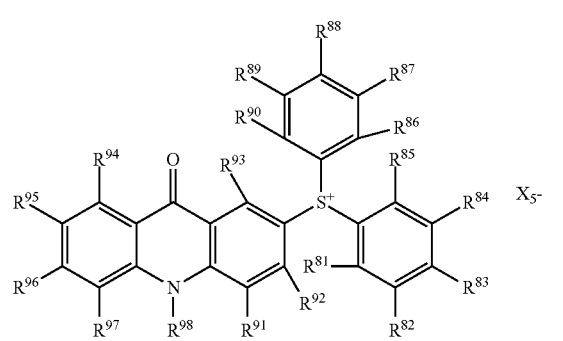

wherein $R^{81}$, $R^{82}$, $R^{83}$, $R^{84}$, $R^{85}$, $R^{86}$, $R^{87}$, $R^{88}$, $R^{89}$, and $R^{90}$ each independently represent a hydrogen atom or a halogen atom;

$R^{91}$, $R^{92}$, $R^{93}$, $R^{94}$, $R^{95}$, $R^{96}$, and $R^{97}$ represent a hydrogen atom;

$R^{98}$ represents a hydroxyl-substituted arylalkyl group having 7 to 20 carbon atoms; and $X_5^-$ represents a monovalent anion.

7. A photo-acid generator composition comprising the aromatic sulfonium salt compound according to claim 6.

8. A cationic polymerization initiator composition comprising the aromatic sulfonium salt compound according to claim 6.

* * * * *